US007928186B2

(12) United States Patent
Chang

(10) Patent No.: US 7,928,186 B2
(45) Date of Patent: Apr. 19, 2011

(54) CELL PERMEABLE BIOACTIVE PEPTIDE CONJUGATES

(75) Inventor: Jaw-Kang Chang, San Carlos, CA (US)

(73) Assignee: Phoenix Pharmaceuticals, Inc., Burlingame, CA (US)

( * ) Notice: Subject to any disclaimer, the term of this patent is extended or adjusted under 35 U.S.C. 154(b) by 269 days.

(21) Appl. No.: 11/890,046

(22) Filed: Aug. 2, 2007

(65) Prior Publication Data
US 2009/0030178 A1 Jan. 29, 2009

Related U.S. Application Data

(60) Provisional application No. 60/835,365, filed on Aug. 2, 2006.

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl. ........................................ 530/324; 530/325

(58) Field of Classification Search ........................ None
See application file for complete search history.

(56) References Cited

U.S. PATENT DOCUMENTS 5,441,936 A 8/1995 Houghten et al.
5,968,512 A * 10/1999 Tuomanen et al. ......... 424/150.1

OTHER PUBLICATIONS

Frankel et al. Activity of synthetic peptides from the Tat protein of human immunodeficiency virus type 1. PNAS, Oct. 1989. pp. 7397-7401.*
Bulaj. Formation of disulfide bonds in proteins and peptides. Biotechnology Advances. (2005), vol. 23, pp. 87-92.*
Annis et al. Disulfide Bond Formation in Peptides. Methods in Enzymology, vol. 289, pp. 198-221.*
French et al. What is a Conservative Substitution? J Mol Evol. 1983, pp. 171-175.*
Annis et al. Disulfide Bond Formation in Peptides. Current protocols in Protein Science. 2001. 18.6.1-18.6.19.*
Bachvarov et al., Agonist-Induced Receptor Internalization; The Journal of Pharmacology and Experimental Therapeutics; vol. 297, No. 1, 19-26 (2001).
Bonny et al., Cell-Permeable Peptide Inhibitors of JNK; Diabetes, vol. 50, 77-82; Switzerland (Jan. 2001).
Borsello et al., A peptide inhibitor of c-Jun N-terminal kinase protects against excitotoxity and cerebral ischemia; Nature Medicine, vol. 9,1180-1186, (Sep. 2003).
Boykins et al., Cutting Edge: A Short Polypeptide Domain of HIV-1-Tat Protein Mediates Pathogenesis, The Journal of Immunology, 163:15-20 (1999).
Brand et al., HIV-1 Tat Protein Is a Substrate and Inhibitor of PKR; The Journal of Biological Chemistry, vol. 272, No. 13, 8388-8395 (Mar. 28, 1997).

Chang et al., Dissecting Endogenous 5-HT2c Receptor Signaling Pathways; The Journal of Biological Chemistry, vol. 275, No. 10, 7021-7029, (Mar. 10, 2000).
Farrell et al., Ingibition of Epstein-Barr virus-induced growth proliferation by anuclear antigen EBNA2-Tat peptide; PNAS, vol. 101 No. 13, 4625-4630 (Mar. 30, 2004).
Feligioni et al., Tat-Evoked Ach Release in Human and Rat Brain; The Journal of Neuroscience, vol. 23 No. 17, 6810-6818 (Jul. 30, 2003).
Joliot et al., Transduction peptides' from technology to physiology; Nature Cell Biology, vol. 6 No. 3, 189-196 (Mar. 2004).
Kaneto et al., Possible novel therapy for diabetes with cell-permeable JNK-inhibitory peptide; Nature Medicine, vol. 10 No. 10, 1128-1132 (Oct. 2004).
Kaushik et al., Anti-tar PNA inhibits HIV-1 in Culture; Journal of Virology, vol. 76 No. 8, 3881-3891 (Apr. 2002).
Kubota et al., NF-kB Inhibition Reduces Sleep; Am J Physiol Regulatory Intergrative Comp Physiol, vol. 279, R404-R413, (Feb. 25, 2000).
Lin et al., Nuclear Translocation of NF-kB Inhibited by Cell-permeable Peptide; The Journal of Biological Chemistry, vol. 270 No. 24, 14255-14258 (Jun. 16, 1995).
Liu et al., Peptide-directed Suppression of Cytokine Response; The Journal of Biological Chemistry, vol. 275 No. 22,16774-16778 (Jun. 2, 2000).
Lu et al., Angiotensin II-Induced Nuclear Targeting of the Angiotensin Type 1 Receptor in Brain Neurons; Endocrinology, vol. 139 No. 1, 365-375 (1998).
Takenobu et al., p53 Protein Transduction Therapy; Molecular Cancer Therapeutics, vol. 1, 1043-1049 (Oct. 2002).
Wang et al., Cell Permeable Bcl-2 Binding Peptides; Cancer Research 60, 1498-1502 (Mar. 15, 2000).
Weihofen et al., Structure of HIV-1 Tat(1-91) bound to DPPIV; JBC Papers in Press., 13 total pages, (Jan. 28, 2005).
Y. Hashimoto, et al., Proc. Natl. Acad. Sci. U.S.A., 98, 6336 (2001).
"Site-specific effects of apelin-13 in the rat medulla oblongata on arterial pressure and respiration" Auton Neurosci. 101(1-2):32-8 (2002).
"Ghrelin causes hyperphagia and obesity in rats", A.M. Wren et al. Diabetes 50(11):2540-7 2001.
"Gut hormone PYY(3-36) physiologically inhibits food intake", R.L. Batterham et al. Nature 418(6898):650-654 (2002).
"Enhanced inhibitory feeding response to alpha-melanocyte stimulating hormone in the diet-induced obese rat", M.J. Hansen, et al., Brain Res. 892(1):130-137 (2001). "Inhibition of growth of MDA-MB-468 estrogen-independent human breast carcinoma by bombesin/gastrin-releasing . . . ", Zsuzsanna et al. Cancer, vol. 88, Issue 6, 1384-1392 (2000).
"Hemodynamic Effects of Human Atrial Natriuretic Peptide After Modified Fontan Procedure", Takeshi Hiramatsu, MD, et al., Ann Thorac Surg 1998;65:761-764.

(Continued)

*Primary Examiner* — Marcela M Cordero Garcia
(74) *Attorney, Agent, or Firm* — Craig R. Miles; CR Miles, P.C.

(57) ABSTRACT

Cell permeable bioactive peptide conjugates having a first bioactive peptide region coupled to a second transport peptide region allowing transfer of the first bioactive peptide region and the second transport peptide region across biological membranes to enter intact living cells for regulation of biological responses.

11 Claims, 26 Drawing Sheets

OTHER PUBLICATIONS

"Encapsulated transgene cells attenuate hypertension, cardiac hypertrophy and enhance renal . . . " Li-Guo Chen et al. The Journal of Gene medicine 6:786-797 (2004).

"Cardiovascular Effects of Brain Natriuretic Peptide in Essential Hypertension", Giorgio La Villa, et al., Hypertension, 25, 1053-1057 (1995).

Kristensen, P. et al., Nature 393, 72-76 (1998).

J Biol Chem. Feb. 15, 1991;266(5):2897-902.

"Identification of Receptors for Neuromedin U and its Role in Feeding" Howard et al. Nature 406, 70-75 (Jul. 6, 2000).

"Systemic administration of growth hormone-releasing peptide activates hypothalamic arcuate neurons", S.L. Dickson, et al., Neuroscience. Mar. 1993;53(2):303-6.

"Mitochondrial coupling factor 6 as a potent endogenous vasoconstrictor" Tomohiro Osanai, et al., J. Clin. Invest. 108(7) 1023-1030 (2001).

Norvartis Pharmaceuticals Corporation, East Hanover, New Jersey, Publication T2002-82 (2002).

"Hemodynamic actions of systemically injected pituitary adenylate cyclase activating . . . ", E.J.Whalen, et al., European Journal of Pharm. vol. 366, No. 2, pp. 205-215 (1999).

"An antiangiogenic urokinase-derived peptide combined with tamoxifen decreases tumor growth and metastasis . . . " Y. Guo, et al, Cancer Res. 202 Aug. 15; 62(16):4678-84.

Larsen PJ, Vrang N, Tang-Christensen M. Curr Pharm Des. 2003;9 (17):1373-82.

Currier, E.A., et al., Biochemical Pharmacology, vol. 67, No. 7.

Young LH, et al. Am J Physiol Heart Circ Physiol. 279(4):H1453-9 (2000).

Zaidi, M. et al., Critical Reviews in Clinical Laboratory Sciences 28, No. 2, 109 (1990).

"Melanin-concentrating hormone: a functional melanocortin antagonist in the hypothalamus" David S. Ludwig, et al., Am J Physiol Endocrinol Metab 274: E627-E633, 1998.

"Adrenomedullin: a smart road from pheochromocytoma to treatment of pulmonary hypertension." M. Westphal, M. Booke and A.T. Dinh-Xuan Eur Respir J 24;518:520 (2004).

Koken et al. Intracellular Analysis of In Vitro Modified HIV Tat Protein. The Journal of Biological Chemistry, 1994; 269(11), pp. 8366-8375.

Löhr et al. Small HIV-1-Tat Peptides Inhibit HIV Replication in Cultured T-cells. Biochemical and Biophysical Research Communications, 2003; 300, pp. 609-613.

Tian et al. Continuous Solid-Phase Synthesis and Disulfide Cyclization of Peptide-PNA-Peptide Chimeras. Organic Letters, 2002; 4(23), pp. 4013-4016.

* cited by examiner

Arg Lys Lys Arg Arg Gln Arg Arg Arg

FIG. 1

Arg Gln Ile Lys Ile Trp Phe Gln Asn Arg Arg Met Lys Trp Lys Lys

FIG. 2

Cys Cys Phe His Cys Gln Val Cys Phe Ile Thr Lys Ala Leu Gly Ile Ser
30  31       34  35      37      40            45

Tyr Gly Arg Lys Lys Arg Arg Gln Arg Arg Ala His Gln Asn Ser Gln Thr
        50              55              60

His Gln Ala Ser Leu Ser Lys Gln Pro Thr Ser Gln Pro Arg Gly Asp
65           70              75                      80

Pro Thr Gly Pro Lys Glu
            85  86

FIG. 3

```
Acm  Trt       Trt Acm Trt      Trt          tBu Boc                    tBu
 |    |         |   |   |        |            |   |                      |
Cys  Cys Phe His Cys Gln Val Cys Phe Ile Thr Lys Ala Leu Gly Ile        Ser
30   31          34  35      37          40                  45 tBu      Pbf Boc Boc Pbf Pbf Trt Pbf Pbf Pbf     Trt Trt Trt tBu Trt tBu
 |        |   |   |   |   |   |   |   |   |      |   |   |   |   |   |
Tyr  Gly Arg Lys Lys Arg Arg Gln Arg Arg Arg Ala His Gln Asn Ser Gln Thr
              50              55                      60

Trt  Trt     tBu     tBu Boc Trt     Bzl Bzl         Tos     OcHex
 |    |       |       |   |   |       |   |           |       |
His  Gln Ala Ser Leu Ser Lys Gln Pro Thr Ser Gln Pro Arg Gly Asp
65                    70              75                      80

Bzl         Clz OcHex
       |           |   |
Pro  Thr Gly Pro Lys Glu-resin
                 85  86
```

FIG. 4

```
Acm  SH          Acm         SH
 |    |           |           |
Cys  Cys Phe His Cys Gln Val Cys Phe Ile Thr Lys Ala Leu Gly Ile Ser
30   31          34  35      37          40                  45

Tyr  Gly Arg Lys Lys Arg Arg Gln Arg Arg Arg Ala His Gln Asn Ser Gln Thr
              50              55                      60

His  Gln Ala Ser Leu Ser Lys Gln Pro Thr Ser Gln Pro Arg Gly Asp
65                    70              75                      80

Pro  Thr Gly Pro Lys Glu
                 85  86
```

FIG. 5

```
Acm                    Acm
 |                      |
Cys Cys Phe His Cys Gln Val Cys Phe Ile Thr Lys Ala Leu Gly Ile Ser
30  31          34  35      37          40                      45
 |                           |
 S───────────────────────────S

Tyr Gly Arg Lys Lys Arg Arg Gln Arg Arg Arg Ala His Gln Asn Ser Gln Thr
            50                  55                  60

His Gln Ala Ser Leu Ser Lys Gln Pro Thr Ser Gln Pro Arg Gly Asp
65                  70                  75                  80

Pro Thr Gly Pro Lys Glu
                85  86
```

FIG. 6

```
S───────────────S
 |               |
Cys Cys Phe His Cys Gln Val Cys Phe Ile Thr Lys Ala Leu Gly Ile Ser
30  31          34  35      37          40                      45
 |                           |
 S───────────────────────────S

Tyr Gly Arg Lys Lys Arg Arg Gln Arg Arg Arg Ala His Gln Asn Ser Gln Thr
            50                  55                  60

His Gln Ala Ser Leu Ser Lys Gln Pro Thr Ser Gln Pro Arg Gly Asp
65                  70                  75                  80

Pro Thr Gly Pro Lys Glu
                85  86
```

FIG. 7

| Cys | Cys | Phe | His | Cys | Gln | Val | Cys | Phe | Ile | Thr | Lys | Ala | Leu | Gly | Ile | Ser |
| 30 | 31 | | | 34 | 35 | | 37 | | | 40 | | | | | | 45 |

| Tyr | Gly | Arg | Lys | Lys | Arg | Arg | Gln | Arg | Arg | Arg |
| | | | 50 | | | | | 55 | | 57 |

FIG. 8

| Cys | Phe | His | Cys | Gln | Val | Cys | Phe | Ile | Thr | Lys | Ala | Leu | Gly | Ile | Ser |
| 31 | | | 34 | 35 | | 37 | | | 40 | | | | | | 45 |

| Tyr | Gly | Arg | Lys | Lys | Arg | Arg | Gln | Arg | Arg | Arg |
| | | | 50 | | | | | 55 | | 57 |

FIG. 9

| Phe | His | Cys | Gln | Val | Cys | Phe | Ile | Thr | Lys | Ala | Leu | Gly | Ile | Ser |
| 32 | | 34 | 35 | | 37 | | | 40 | | | | | | 45 |

| Tyr | Gly | Arg | Lys | Lys | Arg | Arg | Gln | Arg | Arg | Arg |
| | | | 50 | | | | | 55 | | 57 |

FIG. 10

| His | Cys | Gln | Val | Cys | Phe | Ile | Thr | Lys | Ala | Leu | Gly | Ile | Ser |
| 33 | 34 | 35 | | 37 | | | 40 | | | | | | 45 |

| Tyr | Gly | Arg | Lys | Lys | Arg | Arg | Gln | Arg | Arg | Arg |
| | | | 50 | | | | | 55 | | 57 |

FIG. 11

| Cys | Gln | Val | Cys | Phe | Ile | Thr | Lys | Ala | Leu | Gly | Ile | Ser |
| 34 | 35 | | 37 | | | 40 | | | | | | 45 |

| Tyr | Gly | Arg | Lys | Lys | Arg | Arg | Gln | Arg | Arg | Arg |
| | | | 50 | | | | | 55 | | 57 |

FIG. 12

Ac Lys Pro Ser Ser Pro Pro Glu Glu Arg Lys Lys Arg Arg Gln Arg Arg Arg

FIG. 23

Met Ala Pro Arg Gly Phe Ser Cys Leu Leu Leu Leu Thr Ser Glu Ile Asp Leu Pro Val Lys Arg Arg Ala Arg Lys Lys Arg Arg Gln Arg Arg Arg

FIG. 24

Arg Lys Lys Arg Arg Gln Arg Arg Arg Met Ala Pro Arg Gly Phe Ser Cys Leu Leu Leu Leu Thr Ser Glu Ile Asp Leu Pro Val Lys Arg Arg Ala

FIG. 25 pGlu Arg Pro Arg Leu Ser His Lys Gly Pro Met Pro Phe Arg Lys Lys Arg Arg Gln Arg Arg Arg

FIG. 26

Leu Val Gln Pro Arg Gly Ser Arg Asn Gly Pro Gly Pro Trp Gln Gly Gly Arg Arg Lys Phe Arg Arg Gln Arg Pro Arg Leu Ser His Lys Gly Pro Met Pro Phe Arg Lys Lys Arg Arg Gln Arg Arg Arg

FIG. 27

Gly Ser Ser(Des Octanoyl) Phe Leu Ser Pro Glu His Gln Arg Val Gln Gln Arg Lys Glu Ser Lys Lys Pro Pro Ala Lys Leu Gln Pro Arg Arg Lys Lys Arg Arg Gln Arg Arg Arg

FIG. 28

Gly Ser Ser(Octanoyl) Phe Leu Ser Pro Glu His Gln Lys Ala Gln
Gln Arg Lys Glu Ser Lys Lys Pro Pro Ala Lys Leu Gln Pro Arg Arg
Lys Lys Arg Arg Gln Arg Arg Arg

FIG. 29

Gly Ser Ser(Octanoyl) Phe Leu Ser Pro Glu His Gln Arg Val Gln
Gln Arg Lys Glu Ser Lys Lys Pro Pro Ala Lys Leu Gln Pro Arg Arg
Lys Lys Arg Arg Gln Arg Arg Arg

FIG. 30

Asp Arg Val Tyr Ile His Pro Phe Arg Lys Lys Arg Arg Gln Arg Arg Arg

FIG. 31

Asp Arg Val Tyr Ile His Pro Arg Lys Lys Arg Arg Gln Arg Arg Arg

FIG. 32

Val Tyr Ile His Pro Phe Arg Lys Lys Arg Arg Gln Arg Arg Arg

FIG. 33

His D Trp D Lys Trp D Phe Lys Arg Lys Lys Arg Arg Gln Arg Arg Arg

FIG. 34

Ile Lys Pro Glu Ala Pro Gly Glu Asp Ala Ser Pro Glu Glu Leu Asn
Arg Tyr Tyr Ala Ser Leu Arg His Tyr Leu Asn Leu Val Thr Arg Gln
Arg Tyr Arg Lys Lys Arg Arg Gln Arg Arg Arg

FIG. 35

Arg Lys Lys Arg Arg Gln Arg Arg Arg Ile Lys Pro Glu Ala Pro
Gly Glu Asp Ala Ser Pro Glu Glu Leu Asn Arg Tyr Tyr Ala Ser
Leu Arg His Tyr Leu Asn Leu Val Thr Arg Gln Arg Tyr

FIG. 36

Ac Ser Tyr Ser Met Glu His Phe Arg Trp Gly Lys Pro Val Arg
Lys Lys Arg Arg Gln Arg Arg Arg

FIG. 37

Asp Phe Asp Met Leu Arg Cys Met Leu Gly Arg Val Tyr Arg Pro Cys
          |                                                    |
          S————————————————————————————————————————————————————S
Trp Gln Val Arg Lys Lys Arg Arg Gln Arg Arg Arg

FIG. 38 pGlu Gln Arg Leu Gly Asn Gln Trp Ala Val Gly His Leu Met Arg
Lys Lys Arg Arg Gln Arg Arg Arg

FIG. 39

Gly Ile Val Glu Gln Cys Cys Thr Ser Ile Cys Ser Leu Tyr Gln
Leu Glu Asn Tyr Cys Asn Phe Val Asn Gln His Leu Cys Gly Ser
His Leu Val Glu Ala Leu Tyr Leu Val Cys Gly Glu Arg Gly Phe
Phe Tyr Thr Pro Lys Thr Arg Lys Lys Arg Arg Gln Arg Arg Arg

FIG. 40

```
Ser Leu Arg Arg Ser Ser Cys Phe Gly Gly Arg Met Asp Arg Ile Gly
                        |
                        S ─────────────────────────────────────
Ala Gln Ser Gly Leu Gly Cys Asn Ser Phe Arg Tyr Arg Lys Lys Arg
                        |
 ───────────────────────S
Arg Gln Arg Arg Arg
```

FIG. 41

```
Ser Pro Lys Met Val Gln Gly Ser Gly Cys Phe Gly Arg Lys Met Asp
                                    |
                                    S ─────────────────────────
Arg Ile Ser Ser Ser Ser Gly Leu Gly Cys Lys Val Leu Arg Arg His
                                    |
 ───────────────────────────────────S
Arg Lys Lys Arg Arg Gln Arg Arg Arg
```

FIG. 42

```
Asn Ser Lys Met Ala His Ser Ser Ser Cys Phe Gly Gln Lys Ile Asp
                                    |
                                    S ─────────────────────────
Arg Ile Gly Ala Val Ser Arg Leu Gly Cys Asp Gly Leu Arg Leu Phe
                                    |
 ───────────────────────────────────S
Arg Lys Lys Arg Arg Gln Arg Arg Arg
```

FIG. 43

Ser Ser Arg Arg Cys Val Arg Leu His Glu Ser Cys Leu Gly Gln Gln
Val Pro Cys Cys Asp Pro Cys Ala Thr Cys Tyr Cys Arg Phe Phe Asn
Ala Phe Cys Tyr Cys Arg Lys Leu Gly Thr Ala Met Asn Pro Cys Ser
Arg Thr Arg Lys Lys Arg Arg Gln Arg Arg Arg

FIG. 45

Arg Lys Lys Arg Arg Gln Arg Arg Arg His Ala Glu Gly Thr Phe Thr
Ser Asp Val Ser Ser Tyr Leu Glu Gly Gln Ala Ala Lys Glu Phe Ile
Ala Trp Leu Val Lys Gly Arg Gly

FIG. 46

His Ala Glu Gly Thr Phe Thr Ser Asp Val Ser Ser Tyr Leu Glu Gly
Gln Ala Ala Lys Glu Phe Ile Ala Trp Leu Val Lys Gly Arg Gly Arg
Lys Lys Arg Arg Gln Arg Arg Arg

FIG. 47

Glu Gly Thr Phe Thr Ser Asp Leu Ser Lys Gln Met Glu Glu Glu Ala
Val Arg Leu Phe Ile Glu Trp Leu Lys Asn Gly Gly Pro Ser Ser Gly
Ala Pro Pro Pro Ser Arg Lys Lys Arg Arg Gln Arg Arg Arg

FIG. 48

Arg Lys Lys Arg Arg Gln Arg Arg Arg Glu Gly Thr Phe Thr Ser Asp
Leu Ser Lys  Gln Met Glu Glu Glu Ala Val Arg Leu Phe Ile Glu Trp
Leu Lys Asn Gly Gly Pro Ser Ser Gly Ala Pro Pro Pro Ser NH2

FIG. 49

His Ser Asp Gly Thr Phe Thr Ser Asp Leu Ser Lys Gln Met Glu Glu
Glu Ala Val Arg Leu Phe Ile Glu Trp Leu Lys Asn Gly Gly Pro Ser
Ser Gly Ala Pro Pro Pro Ser Arg Lys Lys Arg Arg Gln Arg Arg Arg

FIG. 50

Glu Ala Glu Asp Leu Gln Val Gly Gln Val Glu Leu Gly Gly Gly Pro
Gly Ala Gly Ser Leu Gln Pro Leu Ala Leu Glu Gly Ser Leu Gln Arg
Lys Lys Arg Arg Gln Arg Arg Arg

FIG. 51

Val Thr His Arg Leu Ala Gly Leu Leu Ser Arg Ser Gly Gly Val Val
Lys Asn Asn Phe Val Pro Thr Asn Val Gly Ser Lys Ala Phe Arg Lys
Lys Arg Arg Gln Arg Arg Arg

FIG. 52

Tyr Arg Gln Ser Met Asn Asn Phe Gln Gly Leu Arg Ser Phe Gly Cys
                                                              |
                                                              S—
Arg Phe Gly Thr Cys Thr Val Gln Lys Leu Ala His Gln Ile Tyr Gln
                      |
——————————— S
Phe Thr Asp Lys Asp Lys Asp Asn Val Ala Pro Arg Ser Lys Ile Ser
Pro Gln Gly Tyr Arg Lys Lys Arg Arg Gln Arg Arg Arg

FIG. 53

Ala Arg Leu Asp Val Ala Ser Glu Phe Arg Lys Lys Trp Asn Lys Trp
Ala Leu Ser Arg Arg Lys Lys Arg Arg Gln Arg Arg Arg

FIG. 54

His Ser Asp Gly Ile Phe Thr Asp Ser Tyr Ser Arg Tyr Arg Lys Gln
Met Ala Val Lys Lys Tyr Leu Ala Ala Val Leu Gly Lys Arg Tyr Lys
Gln Arg Val Lys Asn Lys Arg Lys Lys Arg Arg Gln Arg Arg Arg

FIG. 55

His Ser Asp Gly Ile Phe Thr Asp Ser Tyr Ser Arg Tyr Arg Lys Gln
Met Ala Val lys Lys Tyr Leu Ala Ala Val Leu Arg Lys Lys Arg Arg
Gln Arg Arg Arg

FIG. 56

Cys Ser Asn Leu Ser Thr Cys Val Leu Gly Lys Leu Ser Gln Glu Leu
 |                         |
 S ─────────────────────── S
His Lys Leu Gln Thr Tyr Pro Arg Thr Asn Thr Gly Ser Gly Thr Pro
Arg Lys Lys Arg Arg Gln Arg Arg Arg

FIG. 57

Val Leu Gly Lys Leu Ser Gln Glu Leu His Lys Leu Gln Thr Tyr Pro
Arg Thr Asn Thr Gly Ser Gly Thr Pro Arg Lys Lys Arg Arg Gln Arg
Arg Arg

FIG. 58

Phe Arg Val Asp Glu Glu Phe Gln Ser Pro Phe Ala Ser Gln Ser Arg
Gly Tyr Phe Leu Phe Arg Pro Arg Asn Arg Lys Lys Arg Arg Gln Arg
Arg Arg

FIG. 59

Tyr Phe Leu Phe Arg Pro Arg Asn Arg Lys Lys Arg Arg Gln Arg Arg
Arg

FIG. 60

Tyr Lys Val Asn Glu Tyr Gln Gly Pro Val Ala Pro Ser Gly Gly Phe
Phe Leu Phe Arg Pro Arg Asn Arg Lys Lys Arg Arg Gln Arg Arg Arg

FIG. 61

Arg Lys Lys Arg Arg Gln Arg Arg Arg D Phe Cys Phe D Trp Lys Thr
Cys Thr ol

FIG. 62

Arg Lys Lys Arg Arg Gln Arg Arg Arg D PHe Cys  Tyr D Trp Lys Thr
Cys Thr ol

FIG. 63 pGlu Thr Ser Gly Gly Pro Val Asp Ala Ser Ser GluTyr Gln Gln Glu
Leu Glu Arg Glu Leu Phe Lys Leu Lys Gln Met Phe Gly Asn Ala Asp
Met Asn Thr Phe Pro Thr Phe Lys Phe Glu Asp Pro Lys Phe Glu Val
Ile Glu Lys Pro Gln Ala Arg Lys Lys Arg Arg Gln Arg Arg Arg

FIG. 64

Asn Lys Glu Leu Asp Pro Ile Gln Lys Leu Phe Val Asp Lys Ile Arg
Glu Tyr Lys Ser Lys Arg Gln Thr Ser Gly Gly Pro Val Asp Ala Ser
Ser Glu Tyr Gln Gln Glu Leu Glu Arg Glu Leu Phe Lys Leu Lys Gln
Met Phe Gly Asn Ala Asp Met Asn Thr Phe Pro Thr Phe Lys Phe Glu
Asp Pro Lys Phe Glu Val Ile Glu Lys Pro Gln Ala Asn Arg Lys Lys
Arg Arg Gln Arg Arg Arg

FIG. 65

Ac Lys Pro Ser Ser Pro Pro Glu Glu Arg Gln Ile Lys Ile Trp Phe
Gln Asn Arg Arg Met Lys Trp Lys Lys

FIG. 66

Met Ala Pro Arg Gly Phe Ser Cys Leu Leu Leu Leu Thr Ser Glu Ile
Asp Leu Pro Val Lys Arg Arg Ala Arg Gln Ile Lys Ile Trp Phe Gln
Asn Arg Arg Met Lys Trp Lys Lys

FIG. 67

Arg Gln Ile Lys Ile Trp Phe Gln Asn Arg Arg Met Lys Trp Lys Lys
Met Ala Pro Arg Gly Phe Ser Cys Leu Leu Leu Leu Thr Ser Glu Ile
Asp Leu Pro Val Lys Arg Arg Ala

FIG. 68 pGlu Arg Pro Arg Leu Ser His Lys Gly Pro Met Pro Phe Arg Gln Ile
Lys Ile Trp Phe Gln Asn Arg Arg Met Lys Trp Lys Lys

FIG. 69

Leu Val Gln Pro Arg Gly Ser Arg Asn Gly Pro Gly Pro Trp Gln Gly
Gly Arg Arg Lys Phe Arg Arg Gln Arg Pro Arg Leu Ser His Lys Gly
Pro Met Pro Phe Arg Gln Ile Lys Ile Trp Phe Gln Asn Arg Arg Met
Lys Trp Lys Lys

FIG. 70

Gly Ser Ser (Des Octanoyl) Phe Leu Ser Pro Glu His Gln Arg Val
Gln Gln Arg Lys Glu Ser Lys Lys Pro Pro Ala Lys Leu Gln Pro Arg
Arg Gln Ile Lys Ile Trp Phe Gln Asn Arg Arg Met Lys Trp Lys Lys

FIG. 71

Gly Ser Ser(Octanoyl) Phe Leu Ser Pro Glu His Gln Lys Ala Gln Gln
Arg Lys Glu Ser Lys Lys Pro Pro Ala Lys Leu Gln Pro Arg Arg Gln Ile
Lys Ile Trp Phe Gln Asn Arg Arg Met Lys Trp Lys Lys

FIG. 72

Gly Ser Ser(Octanoyl) Phe Leu Ser Pro Glu His Gln Arg Val Gln Gln
Arg Lys Glu Ser Lys Lys Pro Pro Ala Lys Leu Gln Pro Arg Arg Gln Ile
Lys Ile Trp Phe Gln Asn Arg Arg Met Lys Trp Lys Lys

FIG. 73

Asp Arg Val Tyr Ile His Pro Phe Arg Gln Ile Lys Ile Trp Phe Gln
Asn Arg Arg Met Lys Trp Lys Lys

FIG. 74

Asp Arg Val Tyr Ile His Pro Arg Gln Ile Lys Ile Trp Phe Gln Asn
Arg Arg Met Lys Trp Lys Lys

FIG. 75

Val Tyr Ile His Pro Phe Arg Gln Ile Lys Ile Trp Phe Gln Asn Arg
Arg Met Lys Trp Lys Lys

FIG. 76

His D Trp D Lys Trp D Phe Arg Gln Ile Lys Ile Trp Phe Gln Asn Arg
Arg Met Lys Trp Lys Lys

FIG. 77

Ile Lys Pro Glu Ala Pro Gly Glu Asp Ala Ser Pro Glu Glu Leu Asn
Arg Tyr Tyr Ala Ser Leu Arg His Tyr Leu Asn Leu Val Thr Arg Gln
Ile Lys Ile Trp Phe Gln Asn Arg Arg Met Lys Trp Lys Lys

FIG. 78

Arg Gln Ile Lys Ile Trp Phe Gln Asn Arg Arg Met Lys Trp Lys Lys
Ile Lys Pro Glu Ala Pro Gly Glu Asp Ala Ser Pro Glu Glu Leu Asn
Arg Tyr Tyr Ala Ser Leu Arg His Tyr Leu Asn Leu Val Thr Arg Gln
Arg Tyr

FIG. 79

Ac Ser Tyr Ser Met Glu His Phe Arg Trp Gly Lys Pro Val Arg Gln
Ile Lys Ile Trp Phe Gln Asn Arg Arg Met Lys Trp Lys Lys

FIG. 80

Asp Phe Asp Met Leu Arg Cys Met Leu Gly Arg Val Tyr Arg Pro Cys
                    |                                           |
                    S ——————————————————————————————————————— S
Trp Gln Val Arg Gln Ile Lys Ile Trp Phe Gln Asn Arg Arg Met Lys
Trp Lys Lys

FIG. 81 pGlu Gln Arg Leu Gly Asn Gln Trp Ala Val Gly His Leu Met Arg Gln
Ile Lys Ile Trp Phe Gln Asn Arg Arg Met Lys Trp Lys Lys

FIG. 82

Gly Ile Val Glu Gln Cys Cys Thr Ser Ile Cys Ser Leu Tyr Gln Leu
Glu Asn Tyr Cys Asn Phe Val Asn Gln His Leu Cys Gly Ser His Leu
Val Glu Ala Leu Tyr Leu Val Cys Gly Glu Arg Gly Phe Phe Tyr Thr
Pro Lys Thr Arg Gln Ile Lys Ile Trp Phe Gln Asn Arg Arg Met Lys
Trp Lys Lys

FIG. 83

Ser Leu Arg Arg Ser Ser Cys Phe Gly Gly Arg Met Asp Arg Ile Gly
                          |
                          S————————————————————————————
Ala Gln Ser Gly Leu Gly Cys Asn Ser Phe Arg Tyr Arg Gln Ile Lys
                            |
————————————————————————————S
Ile Trp Phe Gln Asn Arg Arg Met Lys Trp Lys Lys

FIG. 84

Ser Pro Lys Met Val Gln Gly Ser Gly Cys Phe Gly Arg Lys Met Asp
                                    |
                                    S————————————————————
Arg Ile Ser Ser Ser Ser Gly Leu Gly Cys Lys Val Leu Arg Arg His
                                      |
——————————————————————————————————————S
Arg Gln Ile Lys Ile Trp Phe Gln Asn Arg Arg Met Lys Trp Lys Lys

FIG. 85

Asn Ser Lys Met Ala His Ser Ser Ser Cys Phe Gly Gln Lys Ile Asp
                                      |
                                      S————————————————————
Arg Ile Gly Ala Val Ser Arg Leu Gly Cys Asp Gly Leu Arg Leu Phe
                                        |
————————————————————————————————————————S
Arg Gln Ile Lys Ile Trp Phe Gln Asn Arg Arg Met Lys Trp Lys Lys

FIG. 86

Ser Ser Arg Arg Cys Val Arg Leu His Glu Ser Cys Leu Gly Gln Gln
Val Pro Cys Cys Asp Pro Cys Ala Thr Cys Tyr Cys Arg Phe Phe Asn
Ala Phe Cys Tyr Cys Arg Lys Leu Gly Thr Ala Met Asn Pro Cys Ser
Arg Thr Arg Gln Ile Lys Ile Trp Phe Gln Asn Arg Arg Met Lys Trp
Lys Lys

FIG. 88

Arg Gln Ile Lys Ile Trp Phe Gln Asn Arg Arg Met Lys Trp Lys Lys
His Ala Glu Gly Thr Phe Thr Ser Asp Val Ser Ser Tyr Leu Glu Gly
Gln Ala Ala Lys Glu Phe Ile Ala Trp Leu Val Lys Gly Arg Gly

FIG. 89

His Ala Glu Gly Thr Phe Thr Ser Asp Val Ser Ser Tyr Leu Glu Gly
Gln Ala Ala Lys Glu Phe Ile Ala Trp Leu VAl Lys Gly Arg Gly Arg
Gln Ile Lys Ile Trp Phe Gln Asn Arg Arg Met Lys Trp Lys Lys

FIG. 90

Glu Gly Thr Phe Thr Ser Asp Leu Ser Lys Gln Met Glu Glu Glu Ala
Val Arg Leu Phe Ile Glu Trp Leu Lys Asn Gly Gly Pro Ser Ser Gly
Ala Pro Pro Pro Ser Arg Gln Ile Lys Ile Trp Phe Gln Asn Arg Arg
Met Lys Trp Lys Lys

FIG. 91

Arg Gln Ile Lys Ile Trp Phe Gln Asn Arg Arg Met Lys Trp Lys Lys
Glu Gly thr Phe Thr Ser Asp Leu Ser Lys  Gln Met Glu Glu Glu Ala
Val Arg Leu Phe Ile Glu Trp Leu Lys Asn Gly Gly Pro Ser Ser Gly
Ala Pro Pro Pro Ser

FIG. 92

His Ser Asp Gly Thr Phe Thr Ser Asp Leu Ser Lys Gln Met Glu Glu
Glu Ala Val Arg Leu Phe Ile Glu Trp Leu Lys Asn Gly Gly Pro Ser
Ser Gly Ala Pro Pro Pro Ser Arg Gln Ile Lys Ile Trp Phe Gln Asn
Arg Arg Met Lys Trp Lys Lys

FIG. 93

Glu Ala Glu Asp Leu Gln Val Gly Gln Val Glu Leu Gly Gly Gly Pro
Gly Ala Gly Ser Leu Gln Pro Leu Ala Leu Glu Gly Ser Leu Gln Arg
Gln Ile Lys Ile Trp Phe Gln Asn Arg Arg Met Lys Trp Lys Lys

FIG. 94

Val Thr His Arg Leu Ala Gly Leu Leu Ser Arg Ser Gly Gly Val Val
Lys Asn Asn Phe Val Pro Thr Asn Val Gly Ser Lys Ala Phe Arg Gln
Ile Lys Ile Trp Phe Gln Asn Arg Arg Met Lys Trp Lys Lys

FIG. 95

Tyr Arg Gln Ser Met Asn Asn Phe Gln Gly Leu Arg Ser Phe Gly
Cys Arg Phe Gly Thr Cys Thr Val Gln Lys Leu Ala His Gln Ile
```
 |                         |
S ─────────────────────── S
```
Tyr Gln Phe Thr Asp Lys Asp Lys Asp Asn Val Ala Pro Arg Ser
Lys Ile Ser Pro Gln Gly Tyr Arg Gln Ile Lys Ile Trp Phe Gln
Asn Arg Arg Met Lys Trp Lys Lys

FIG. 96

Ala Arg Leu Asp Val Ala Ser Glu Phe Arg Lys Lys Trp Asn Lys Trp
Ala Leu Ser Arg Arg Gln Ile Lys Ile Trp Phe Gln Asn Arg Arg Met
Lys Trp Lys Lys

FIG. 97

His Ser Asp Gly Ile Phe Thr Asp Ser Tyr Ser Arg Tyr Arg Lys Gln
Met Ala Val Lys Lys Tyr Leu Ala Ala Val Leu Gly Lys Arg Tyr Lys
Gln Arg Val Lys Asn Lys Arg Gln Ile Lys Ile Trp Phe Gln Asn Arg
Arg Met Lys Trp Lys Lys

FIG. 98

His Ser Asp Gly Ile Phe Thr Asp Ser Tyr Ser Arg Tyr Arg Lys Gln
Met Ala Val Lys Lys Tyr Leu Ala Ala Val Leu Arg Gln Ile Lys Ile
Trp Phe Gln Asn Arg Arg Met Lys Trp Lys Lys

FIG. 99

Cys Ser Asn Leu Ser Thr Cys Val Leu Gly Lys Leu Ser Gln Glu Leu
His Lys Leu Gln Thr Tyr Pro Arg Thr Asn Thr Gly Ser Gly Thr Pro
Arg Gln Ile Lys Ile Trp Phe Gln Asn Arg Arg Met Lys Trp Lys Lys
Lys Lys Arg Arg Gln Arg Arg Arg

FIG. 100

Val Leu Gly Lys Leu Ser Gln Glu Leu His Lys Leu Gln Thr Tyr Pro
Arg Thr Asn Thr Gly Ser Gly Thr Pro Arg Gln Ile Lys Ile Trp Phe
Gln Asn Arg Arg Met Lys Trp Lys Lys

FIG. 101

Phe Arg Val Asp Glu Glu Phe Gln Ser Pro Phe Ala Ser Gln Ser Arg
Gly Tyr Phe Leu Phe Arg Pro Arg Asn Arg Gln Ile Lys Ile Trp Phe
Gln Asn Arg Arg Met Lys Trp Lys Lys

FIG. 102

Tyr Phe Leu Phe Arg Pro Arg Asn Arg Gln Ile Lys Ile Trp Phe Gln
Asn Arg Arg Met Lys Trp Lys Lys

FIG. 103

Tyr Lys Val Asn Glu Tyr Gln Gly Pro Val Ala Pro Ser Gly Gly Phe
Phe Leu Phe Arg Pro Arg Asn Arg Gln Ile Lys Ile Trp Phe Gln Asn
Arg Arg Met Lys Trp Lys Lys

FIG. 104

Arg Gln Ile Lys Ile Trp Phe Gln Asn Arg Arg Met Lys Trp Lys Lys D
Phe Cys Phe D Trp Lys Thr Cys Thr ol

FIG. 105

Arg Gln Ile Lys Ile Trp Phe Gln Asn Arg Arg Met Lys Trp Lys Lys D
PHe Cys  Tyr D Trp Lys Thr Cys Thr ol

FIG. 106 pGlu Thr Ser Gly Gly Pro Val Asp Ala Ser Ser Glu Tyr Gln Gln Glu
Leu Glu Arg Glu Leu Phe Lys Leu Lys Gln Met Phe Gly Asn Ala Asp
Met Asn Thr Phe Pro Thr Phe Lys Phe Glu Asp Pro Lys Phe Glu Val
lle Glu Lys Pro Gln Ala

FIG. 107

Asn Lys Glu Leu Asp Pro lle Gln Lys Leu Phe Val Asp Lys lle Arg
Glu Tyr Lys Ser Lys Arg Gln Thr Ser Gly Gly Pro Val Asp Ala Ser
Ser Glu Tyr Gln Gln Glu Leu Glu Arg Glu Leu Phe Lys Leu Lys Gln
Met Phe Gly Asn Ala Asp Met Asn Thr Phe Pro Thr Phe Lys Phe Glu
Asp Pro Lys Phe Glu Val lle Glu Lys Pro Gln Ala Asn

FIG. 108

CELL PERMEABLE BIOACTIVE PEPTIDE CONJUGATES

This United States patent application claims the benefit of U.S. Provisional Patent Application No. 60/835,365, filed Aug. 2, 2006, hereby incorporated by reference.

I. BACKGROUND

Cell permeable bioactive peptide conjugates having a first bioactive peptide region coupled to a second transport peptide region allowing transfer of the first bioactive peptide region and the second transport peptide region across biological membranes to enter intact living cells for regulation of biological responses.

Various proteins and protein fragments have been shown to regulate biological responses which are of either therapeutic or research interest, or both. However, a substantial problem in utilizing these proteins, protein fragments, or chemically synthesized peptides to regulate the corresponding intracellular processes can be the level of biological availability, if any, at target receptors in the living cell, whether in-vitro or in-vivo. This lack of biological availability may be due to insolubility, a binding affinity to surrounding substrates that is greater than to the target cell receptor, instability with respect to cleavage, or with respect to modification of the peptide backbone, N-terminus, C-terminus, side chain, or other peptide or chemical moiety.

With respect to proteins or peptides such as insulin or humanin, instability with respect to cleavage or modification can to an extent be overcome by administration by injection into or proximate to the tissue which presents the corresponding binding receptors of the protein or peptide, or by introduction by injection into the circulatory system to be carried to the tissue(s) which present the corresponding binding receptors to the protein or peptide, as shown by the following examples:

Humanin has recently been shown to provide protection against forms of Alzheimer's Disease. Humanin is a 24 amino acid linear polypeptide with a single cysteine at position 8. As with insulin, humanin is rapidly degraded by gastrointestinal enzymes, and thus administration by injection may be the only presently available route to deliver the peptide. "A rescue factor abolishing neuronal cell death by wide spectrum of familial Alzheimer's disease genes and $A^{\beta}$" Y. Hashimoto, T. Niikura, H. Tajima, T. Yasukawa, H. Sudo, Y. Ito, Y. Kita, M. Kawasumi, K. Koumaya, M. Doyu, G. Sobue, T. Koide, S. Tsuji, J. Lang, K. Kurokawa, and I. Nishimoto, Proc. Natl. Acad. Sci. U.S.A., 98, 6336 (2001), hereby incorporated by reference herein.

Apelin peptides are now known to be endogenous ligands at the orphan G-protein coupled receptor, APJ. Apelin and its receptor have been found in the brainstem and shown to have a role in haemodynamic homeostasis. Apelin microinjections into the nucleus tractus solitarius ("NTS") can result in either apnea or decreased phrenic nerve discharge amplitude by up to 30%. Increases of 10-20 mm Hg in arterial pressure can also evoked from microinjection of Apelin into either of the NTS and the RVLM. "Site-specific effects of apelin-13 in the rat medulla oblongata on arterial pressure and respiration" Auton Neurosci. 101(1-2):32-8 (2002), hereby incorporated by reference herein.

In both rodents and humans, ghrelin functions to increase hunger though its action on hypothalamic feeding centers. This makes sense relative to increasing plasma ghrelin concentrations observed during fasting. Additionally, humans injected with ghrelin reported sensations of intense hunger. Ghrelin also appears to suppress fat utilization in adipose tissue, which is somewhat paradoxical considering that growth hormone has the opposite effect. Overall, ghrelin seems to be one of several hormonal signals that communicates the state of energy balance in the body to the brain. "Ghrelin causes hyperphagia and obesity in rats", A. M. Wren et al. Diabetes 50(11):2540-72001, hereby incorporated by reference herein.

Peptide YY(3-36) (PYY(3-36)), a Y2R agonist, is released from the gastrointestinal tract postprandially in proportion to the calorie content of a meal. Peripheral injection of PYY(3-36) in rats inhibits food intake and reduces weight gain. PYY(3-36) also inhibits food intake in mice but not in Y2r-null mice, which suggests that the anorectic effect requires the Y2R. Peripheral administration of PYY(3-36) increases c-Fos immunoreactivity in the arcuate nucleus and decreases hypothalamic Npy messenger RNA. Intra-arcuate injection of PYY(3-36) inhibits food intake. PYY(3-36) also inhibits electrical activity of NPY nerve terminals, thus activating adjacent pro-opiomelanocortin (POMC) neurons. In humans, infusion of normal postprandial concentrations of PYY(3-36) significantly decreases appetite and reduces food intake by 33% over 24 h. Thus, postprandial elevation of PYY(3-36) may act through the arcuate nucleus Y2R to inhibit feeding in a gut-hypothalamic pathway. "Gut hormone PYY(3-36) physiologically inhibits food intake", R. L. Batterham et al. Nature 418(6898):650-654 (2002), hereby incorporated by reference herein.

Intracerebroventricular injections of alpha-MSH in diet-induced obese rats results in significantly enhanced nocturnal inhibitory feeding responses. Significantly greater inhibition of nocturnal feeding by alpha-MSH and reduction in PVN alpha-MSH peptide level, suggests melanocortinergic signalling may be reduced in obesity which may account for the hyperphagia of these animals when presented with a palatable diet. "Enhanced inhibitory feeding response to alpha-melanocyte stimulating hormone in the diet-induced obese rat", M. J. Hansen, M. J. Ball and M. J. Morris, Brain Res. 892(1): 130-137 (2001), hereby incorporated by reference herein.

Xenografts of MDA-MB-468 human breast carcinoma injected subcutaneously for 6 weeks with Bomesin peptides showed powerfully suppressed growth causing a complete regression of 2 tumors. "Inhibition of growth of MDA-MB-468 estrogen-independent human breast carcinoma by bomb-esin/gastrin-releasing peptide antagonists RC-3095 and RC-3940-11", Zsuzsanna et al. Cancer, Vol. 88, Issue 6, 1384-1392 (2000), hereby incorporated by reference herein.

Atrial natriuretic peptide (ANP) has the effects of a vasodilator (including the pulmonary arteries) and a physiologic diuretic. "Hemodynamic Effects of Human Atrial Natriuretic Peptide After Modified Fontan Procedure", Takeshi Hiramatsu, MD, Yasuharu Imai, MD, Yoshinori Takanashi, MD, Kazuhiro Seo, MD, Masatsugu Terada, MD, Makoto Nakazawa, MD Ann Thorac Surg 1998; 65:761-764. Exogenous ANP administration has resulted in numerous physiological responses, including rapid natriuresis, diuresis, and reduction in arterial blood pressure. "Encapsulated transgene cells attenuate hypertension, cardiac hypertrophy and enhance renal function in Goldblatt hypertensive rats" Li-Guo Chen et al. The Journal of Gene medicine 6:786-797 (2004), hereby incorporated by reference herein.

Brain natriuretic peptide delivered by infusion can influence cardiovascular homeostasis mainly by reducing cardiac preload. administration of pharmacological doses of BNP to humans and experimental animals markedly affects systemic hemodynamics and renal function, because it is followed by a reduction of arterial pressure and PVR and an increase in diuresis and natriuresis. "Cardiovascular Effects of Brain Natriuretic Peptide in Essential Hypertension", Giorgio La Villa; Gianni Bisi; Chiara Lazzeri; Caterina Fronzaroli; Laura Stefani; Giuseppe Barletta; Riccarda Del Bene; Gianni Messeri; Gaetano Strazzulla; Franco Franchi, Hypertension, 25, 1053-1057 (1995), hereby incorporated by reference herein.

Intracerebroventricular injection of recombinant CART in rats inhibits normal and starvation-induced feeding and completely blocks the feeding response elicited by NPY. Peripheral leptin administration in obese mice stimulates CART mRNA expression. CART antisera increases feeding in normal rats suggesting that CART is an endogenous regulator of food intake. Kristensen, P. et al., Nature 393, 72-76 (1998), hereby incorporated by reference herein.

CNS administration of Agouti related protein decreased oxygen consumption and decreased the capacity of BAT to expend energy. This reduction in oxygen consumption leading to a reduction in energy expenditure, together with the stimulation in food intake, may be the mechanisms by which Agrp causes an increase in body weight and adiposity. "Chronic CNS administration of Agouti related protein (Agrp) reduces energy expenditure", C J Small, Y L Liu, S A Stanley, I P Connoley, A Kennedy, M J Stock & S R Bloom, Endocrine Abstracts 3 OC46, hereby incorporated by reference herein.

Exendin (9-39) binds to but does not activate the GLP-1 receptor, and functions as a GLP-1 receptor antagonist Exendin-3, a novel peptide from *Heloderma horridum* venom, interacts with vasoactive intestinal peptide receptors and a newly described receptor on dispersed acini from guinea pig pancreas. Exendin (9-39) administered acutely has been employed as a GLP-1R antagonists in multiple preclinical studies and in human experiments to probe the consequences of disrupting GLP-1R activation. J Biol. Chem. 1991 Feb. 15; 266(5):2897-902, hereby incorporated by reference herein.

Neuromedin U (NMU) is a neuropeptide with potent activity on smooth muscle which was isolated first from porcine spinal cord and later from other species. It is widely distributed in the gut and central nervous system. Peripheral activities of NMU include stimulation of smooth muscle, increase of blood pressure, alteration of ion transport in the gut, control of local blood flow and regulation of adrenocortical function. NMU is expressed in the ventromedial hypothalamus in the rat brain, and its level is significantly reduced following fasting. Intracerebroventricular administration of NMU markedly suppresses food intake in rats and may indicate that NMU is involved in the central control of feeding. "Identification of Receptors for Neuromedin U and its Role in Feeding" Howard et al. Nature 406, 70-75 (Jul. 6, 2000), hereby incorporated by reference herein.

The systemic administration of synthetic hexapeptide of growth hormone-releasing peptide selectively releases growth hormone in many species including man. Growth hormone-releasing peptide directly stimulates growth hormone release by an action at the level of the pituitary. "Systemic administration of growth hormone-releasing peptide activates hypothalamic arcuate neurons", S. L. Dickson, G. Leng and I. C. Robinson, Neuroscience. 1993 March; 53(2): 303-6, hereby incorporated by reference herein.

Intravenous injection of recombinant coupling factor 6 peptide increased blood pressure, apparently by suppressing prostacyclin synthesis, whereas a specific Ab to coupling factor 6 decreased systemic blood pressure concomitantly with an increase in plasma prostacyclin. Interestingly, the antibody's hypotensive effect could be abolished by treating with the cyclooxygenase inhibitor indomethacin. "Mitochondrial coupling factor 6 as a potent endogenous vasoconstrictor" Tomohiro Osanai, Makoto Tanaka, Takaatsu Kamada, Takao Nakano, Koki Takahashi, Satoko Okada, Kenichi Sirato, Koji Magota, Shiho Kodama, and Ken Okumura, J. Clin. Invest. 108(7) 1023-1030 (2001).

Octreotide injection provides a long-acting pharmacologic action mimicking those of the natural hormone somatostatin. Like somatostatin, octreotide suppresses LH response, gastrin, vasoactive intestinal peptide, secretin, motilin, and pancreatic polypeptide. Norvartis Pharmaceuticals Corporation, East Hanover, N.J., Publication T2002-82 (2002).

Intravenous injection of PACAP-27 can produce dose-dependent decreases in mean arterial blood pressure and hindquarter and mesenteric vascular resistances in saline-treated rats and can produce dose-dependent increases in heart rate. "Hemodynamic actions of systemically injected pituitary adenylate cyclase activating polypeptide-27 in the rat" E. J. Whalen, A. K. Johnson, S. J. Lewis; European Journal of Pharmacology Vol. 365, No. 2, pages 205-215 (1999).

Intra peritoneal injection of an 8-mer peptide derived from the nonreceptor-binding domain of urokinase (A6) has been shown to have antiangiogenic and proapoptotic effects to block the progression of breast cancer in vivo. "An antiangiogenic urokinase-derived peptide combined with tamoxifen decreases tumor growth and metastasis in a syngeneic model of breast cancer" Y. Guo, A. P. Mazar, J. J. Lubrun, and S. A. Rabbani, Cancer Res. 2002 Aug. 15; 62(16):4678-84.

GLP-1 derivatives and analogues to both rodents and man have shown promising effects on food intake and body weight suggesting that such therapies constitute potential anti-obesity treatment. In the central nervous system, pre-proglucagon and hence GLP-1, GLP-2 and OXM are exclusively found in a small population of nerve cells in the nucleus of the solitary tract. These constitute a neural pathway linking the "viscero-sensory" brainstem to hypothalamic nuclei involved in energy homeostasis. Intracerebroventricular administration of all of the three derived peptides robustly decrease food intake. It is evident that central GLP-1 agonism probably in combination with GLP-2 and/or OXM agonism constitute a potential pharmacological tool to reduce food intake and may be also enhance energy expenditure. This and other aspects of the current state of the role of central pre-proglucagon in energy homeostasis are reviewed. Larsen P J, Vrang N, Tang-Christensen M. Curr Pharm Des. 2003; 9(17): 1373-82.

Calcitonin injection suppresses resorption of bone by inhibiting the activity of osteoclasts, a cell type that "digests" bone matrix, releasing calcium and phosphorus into blood. Calcitonin 8-32 can be a potent agonist at the hCTr, with similar efficacy as human calcitonin, and a potency of 11 nM. These results were confirmed in cyclic AMP assays. Responses to calcitonin and PHM-27 could be suppressed by the antagonist salmon calcitonin (8-32). In competition binding studies, salmon calcitonin (8-32), calcitonin, and PHM-27 were each able to inhibit ^1^2^5I-calcitonin from cell membranes containing transiently expressed hCTr. These results indicate that the orphan peptide PHM-27 is a potent agonist at the hCTr. Discovery of novel peptide/receptor interactions: identification of PHM-27 as a potent agonist of the human calcitonin receptor Ma, J.-N., Currier, E. A., Essex, A., Feddock, M., Spalding, T. A., Nash, N. R., Brann, M. R., Burstein, E. S., Biochemical Pharmacology, Vol. 67, No. 7.

C-peptide, a cleavage product of proinsulin to insulin processing, induces nitric oxide (NO)-mediated vasodilation upon injection. C-peptide (70 nmol/kg iv) can significantly improved coronary flow. Moreover, C-peptide enhanced basal NO release from rat aortic segments. Young L H, et al. Am J Physiol Heart Circ Physiol. 279(4):H1453-9 (2000), hereby incorporated by reference herein.

Calcitonin Gene Related Peptide is a potent hypotensive agent and a member of the Calcitonin/CGRP multigene complex. This peptide is 37 amino acids long containing one disulfide bridge. CGRP has been shown upon injection to elevate the flow of blood and enhance the contractibility of the atrium. Zaidi, M. et al., Critical Reviews in Clinical Laboratory Sciences 28, No. 2, 109 (1990), hereby incorporated by reference herein.

Melanin-concentrating hormone (MCH), a neuropeptide expressed in central and peripheral nervous systems which plays an important role in the control of feeding behaviors and energy metabolism. MCH and alpha-MSH exert opposing and antagonistic influences on feeding behavior and the stress response and may function in a coordinate manner to regulate metabolism through a novel mechanism mediated in part by an MCH receptor. Intracerebroventricular administration in rats increased food intake in a dose-dependent manner and lowered plasma glucocorticoid levels through a mechanism involving ACTH. In contrast, alpha-MSH decreased food intake and increased glucocorticoid levels. MCH, at a twofold molar excess, antagonized both actions of alpha-MSH. alpha-MSH, at a threefold molar excess, blocked the orexigenic properties of MCH. MCH did not block alpha-MSH binding or the ability of alpha-MSH to induce cAMP in cells expressing either the MC3 or MC4 receptor, the principal brain alpha-MSH receptor subtypes. These data suggest that MCH and alpha-MSH exert opposing and antagonistic influences on feeding behavior and the stress response and may function in a coordinate manner to regulate metabolism through a novel mechanism mediated in part by an MCH receptor." "Melanin-concentrating hormone: a functional melanocortin antagonist in the hypothalamus" David S. Ludwig, Kathleen G. Mountjoy, Jeffrey B. Tatro, Jennifer A. Gillette, Robert C. Frederich, Jeffrey S. Flier, and Eleftheria Maratos-Flier Am J Physiol Endocrinol Metab 274: E627-E633, 1998, hereby incorporated by reference herein.

Another problem associated with certain peptides such as Adrenomedullin a 52-amino acid peptide hormone with structural homology to calcitonin gene-related peptide may be that administration by aerosol requires a wt/v peptide to carrier which makes the ther FIG. 11 is an embodiment of the invention which comprises a first bioactive peptide region of HIV1 33-48 and a second transport peptide region HIV1 49-57 (SEQ. ID. NO.: 4).

FIG. 12 is an embodiment of the invention which comprises a first bioactive peptide region of HIV1 34-48 and a second transport peptide region HIV1 49-57 (SEQ. ID. NO.: 5).

FIG. 13 is an embodiment of the invention which comprises a first bioactive peptide region of HIV 1 30-48 (Cys 30-Cys31 disulfide) and a second transport peptide region HIV1 49-57 (SEQ. ID. NO.: 6).

FIG. 14 is an embodiment of the invention which comprises a first bioactive peptide region of HIV1 30-48 (Cys 30-Cys 34 disulfide) and a second transport peptide region HIV1 49-57 (SEQ. ID. NO.: 7).

FIG. 15 is an embodiment of the invention which comprises a first bioactive peptide region of HIV1 30-48 (Cys 30-Cys 37 disulfide) and a second transport peptide region HIV1 49-57 (SEQ. ID. NO.: 8).

FIG. 16 is an embodiment of the invention which comprises a first bioactive peptide region of HIV1 30-48 (Cys 31-Cys 34 disulfide) and a second transport peptide region HIV1 49-57 (SEQ. ID. NO.: 9).

FIG. 17 is an embodiment of the invention which comprises a first bioactive peptide region of HIV1 30-48 (Cys 31-Cys 37 disulfide) and a second transport peptide region HIV1 49-57 (SEQ. ID. NO.: 10).

FIG. 18 is an embodiment of the invention which comprises a first bioactive peptide region of HIV1 30-48 (Cys 34-Cys 37 disulfide) and a second transport peptide region HIV1 49-57 (SEQ. ID. NO.: 11).

FIG. 19 is an embodiment of the invention which comprises a first bioactive peptide region of HIV1 30-48 (Cys 30-Cys 31 disulfide)(Cys 34-Cys 37 disulfide) and a second transport peptide region HIV1 49-57 (SEQ. ID. NO.: 12).

FIG. 20 is an embodiment of the invention which comprises a first bioactive peptide region of HIV1 30-48 (Cys 30-Cys 34 disulfide)(Cys 31-Cys 37 disulfide) and a second transport peptide region HIV1 49-57 (SEQ. ID. NO.: 13).

FIG. 21 is an embodiment of the invention which comprises a first bioactive peptide region of HIV1 30-48 (Cys 30-Cys 37 disulfide)(Cys 31-Cys 34 disulfide) and a second transport peptide region HIV1 49-57 (SEQ. ID. NO.: 14).

FIG. 22 is an embodiment of the invention which comprises a first bioactive peptide region of HIV1 30-48 (Cys 30 ACM)(Cys 31-Cys 37 disulfide)(Cys 34 ACM) and a second transport peptide region HIV1 49-57 (SEQ. ID. NO.: 15).

FIG. 23 is the primary sequence of an embodiment of the invention A6(uPA 136-143) C-terminal Tat peptide (SEQ ID NO.: 16).

FIG. 24 is the primary sequence of an embodiment of the invention Humanin C-terminal Tat peptide (SEQ ID NO.: 17).

FIG. 25 is the primary sequence of an embodiment of the invention Humanin N-terminal Tat peptide (SEQ ID NO.: 18).

FIG. 26 is the primary sequence of an embodiment of the invention pGlu1-Apelin-13 C-terminal Tat peptide (SEQ ID NO.: 19).

FIG. 27 is the primary sequence of an embodiment of the invention Apelin-13 C-terminal Tat peptide (SEQ ID NO.: 20).

FIG. 28 is the primary sequence of an embodiment of the invention Ghrelin, desoctyoyl (Human) C-terminal Tat peptide (SEQ ID NO.: 21).

FIG. 29 is the primary sequence of an embodiment of the invention Ghrelin, desoctyoyl (Mouse and Rat) C-terminal Tat peptide (SEQ ID NO.: 22).

FIG. 30 is the primary sequence of an embodiment of the invention Ghrelin, octyoyl (Human) C-terminal Tat peptide (SEQ ID NO.: 23).

FIG. 31 is the primary sequence of an embodiment of the invention Angiotensin II C-terminal Tat peptide (SEQ ID NO.: 24).

FIG. 32 is the primary sequence of an embodiment of the invention Angiotensin I/II (1-7) C-terminal Tat peptide (SEQ ID NO.: 25).

FIG. 33 is the primary sequence of an embodiment of the invention Angiotensin IV C-terminal Tat peptide (SEQ ID NO.: 26).

FIG. 34 is the primary sequence of an embodiment of the invention Growth Hormone Releasing Peptide-6 C-terminal Tat peptide (SEQ ID NO.: 27).

FIG. 35 is the primary sequence of an embodiment of the invention PYY3-36 C-terminal C-terminal Tat peptide (SEQ ID NO.: 28).

FIG. 36 is the primary sequence of an embodiment of the invention PYY3-36 N-terminal Tat peptide (SEQ ID NO.: 29).

FIG. 37 is the primary sequence of an embodiment of the invention MSH, alpha, C-terminal Tat peptide (SEQ ID NO.: 30).

FIG. 38 is the primary sequence of an embodiment of the invention MCH, C-terminal Tat peptide (SEQ ID NO.: 31).

FIG. 39 is the primary sequence of an embodiment of the invention Bromesin, C-terminal Tat peptide (SEQ ID NO.: 32).

FIG. 40 is the primary sequence of an embodiment of the invention Human Insulin-C-terminal Tat peptide (SEQ ID NO.: 33).

FIG. 41 is the primary sequence of an embodiment of the invention Human ANP alpha C-terminal Tat peptide (SEQ ID NO.: 34).

FIG. 42 is the primary sequence of an embodiment of the invention Human BNP C-terminal Tat peptide (SEQ ID NO.: 35).

FIG. 43 is the primary sequence of an embodiment of the invention Rat BNP C-terminal Tat peptide (SEQ ID NO.: 36).

FIG. 45 is the primary sequence of an embodiment of the invention Human AGRP (83-132) C-terminal Tat peptide (SEQ ID NO.: 38).

FIG. 46 is the primary sequence of an embodiment of the invention N-terminal Tat peptide-GLP-1 (7-37) (SEQ ID NO.: 39).

FIG. 47 is the primary sequence of an embodiment of the invention GLP-1 (7-37)—C-terminal Tat peptide (SEQ ID NO.: 40).

FIG. 48 is the primary sequence of an embodiment of the invention Exendin-4 (3-39)-C-terminal Tat peptide (SEQ ID NO.: 41).

FIG. 49 is the primary sequence of an embodiment of the invention N-terminal Tat peptide-Exendin-4 (3-39) (SEQ ID NO.: 42).

FIG. 50 is the primary sequence of an embodiment of the invention Exendin-3-C-terminal Tat peptide (SEQ ID NO.: 43).

FIG. 51 is the primary sequence of an embodiment of the invention Human C-peptide-Tat peptide (SEQ ID NO.: 44).

FIG. 52 is the primary sequence of an embodiment of the invention Human CGRP(8-37)-Tat peptide (SEQ ID NO.: 45).

FIG. 53 is the primary sequence of an embodiment of the invention Human Aredomedullin-C-terminal Tat peptide (SEQ ID NO.: 46).

FIG. 54 is the primary sequence of an embodiment of the invention Human Aredomedullin (AM) Pro-N-20-C-terminal Tat peptide (SEQ ID NO.: 47).

FIG. 55 is the primary sequence of an embodiment of the invention PACAP38-C-terminal Tat peptide (SEQ ID NO.: 48).

FIG. 56 is the primary sequence of an embodiment of the invention PACA27-C-terminal Tat peptide SEQ ID NO.: 49).

FIG. 57 is the primary sequence of an embodiment of the invention Salmon Calcitonin (disulfide bridge Cys1-Cys7)-Tat peptide (SEQ ID NO.: 50).

FIG. 58 is the primary sequence of an embodiment of the invention Salmon Calcitonin (8-32)-C-terminal Tat peptide (SEQ ID NO.: 51).

FIG. 59 is the primary sequence of an embodiment of the invention Human Neuromedin U-C-terminal Tat peptide (SEQ ID NO.: 52).

FIG. 60 is the primary sequence of an embodiment of the invention Porcine Neuromedin-C-terminal Tat peptide (SEQ ID NO.: 53).

FIG. 61 is the primary sequence of an embodiment of the invention Rat Neuromedin-C-terminal Tat peptide (SEQ ID NO.: 54).

FIG. 62 is the primary sequence of an embodiment of the invention N-terminal Tat-Octreotide (SEQ ID NO.: 55).

FIG. 63 is the primary sequence of an embodiment of the invention N-Terminal Tat peptide-Octeotide, Tyr3 (SEQ ID NO.: 56).

FIG. 64 is the primary sequence of an embodiment of the invention Coupling Factor 6 (CF6 Precursor (55-108) C-terminal Tat peptide (SEQ ID NO.: 57).

FIG. 65 is the primary sequence of an embodiment of the invention Coupling Factor 6 (CF^ Precursor (33-108)-C-terminal Tat peptide (SEQ ID NO.: 58).

FIG. 66 is the primary sequence of an embodiment of the invention A6(uPA 136-143)—C-terminal Penetratin peptide (SEQ ID NO.: 59).

FIG. 67 is the primary sequence of an embodiment of the invention Humanin-C-terminal Penetratin peptide (SEQ ID NO.: 60).

FIG. 68 is the primary sequence of an embodiment of the invention N-Terminal Penetratin peptide-Humanin (SEQ ID NO.: 61).

FIG. 69 is the primary sequence of an embodiment of the invention pGlu1-Apelin-C-terminal Penetratin peptide (SEQ ID NO.: 62).

FIG. 70 is the primary sequence of an embodiment of the invention Apelin-C-terminal Penetratin peptide (SEQ ID NO.: 63).

FIG. 71 is the primary sequence of an embodiment of the invention Human Ghrelin, des-octanoyl-Penetratin peptide (SEQ ID NO.: 64).

FIG. 72 is the primary sequence of an embodiment of the invention Mouse/Rat Ghrelin, octanoyl-C-terminal Penetratin peptide (SEQ ID NO.: 65).

FIG. 73 is the primary sequence of an embodiment of the invention Human Ghrelin-C-terminal Penetratin peptide (SEQ ID NO.: 66).

FIG. 74 is the primary sequence of an embodiment of the invention Angiotensin II-C-terminal Penetratin peptide (SEQ ID NO.: 67).

FIG. 75 is the primary sequence of an embodiment of the invention Angiotensin I/II (1-7)-C-terminal Penetratin peptide (SEQ ID NO.: 68).

FIG. 76 is the primary sequence of an embodiment of the invention Angiotensin IV-C-terminal Penetratin peptide (SEQ ID NO.: 69).

FIG. 77 is the primary sequence of an embodiment of the invention Growth Hormone Releasing Peptide-6 (GHRP 6)(D-Lys3)—C-terminal Penetratin peptide (SEQ ID NO.: 70).

FIG. 78 is the primary sequence of an embodiment of the invention Human PYY (3-36)-C-terminal Penetratin peptide (SEQ ID NO.: 71).

FIG. 79 is the primary sequence of an embodiment of the invention C-Terminal Penetratin PYY(3-36) Human (SEQ ID NO.: 72).

FIG. 80 is the primary sequence of an embodiment of the invention MSH, alpha, —C-terminal Penetratin peptide (SEQ ID NO.: 73).

FIG. 81 is the primary sequence of an embodiment of the invention MCH (disulfide bridge Cys7-Cys16)-C-terminal Penetratin peptide (SEQ ID NO.: 74).

FIG. 82 is the primary sequence of an embodiment of the invention Bobesin-C-terminal Penetratin peptide (SEQ ID NO.: 75).

FIG. 83 is the primary sequence of an embodiment of the invention Human Insulin-C-terminal Penetratin peptide (SEQ ID NO.: 76).

FIG. 84 is the primary sequence of an embodiment of the invention Human ANP, alpha (Cys 7-Cys 23)-C-terminal Penetratin peptide (SEQ ID NO.: 77).

FIG. 85 is the primary sequence of an embodiment of the invention Human BNP32 (disulfide bridge Cys10-Cys 26)-C-terminal Penetratin peptide (SEQ ID NO.: 78).

FIG. 86 is the primary sequence of an embodiment of the invention Rat BNP32 (disulfide bridge Cys10-Cys 26)-C-terminal Penetratin peptide (SEQ ID NO.: 79).

FIG. 88 is the primary sequence of an embodiment of the invention Human AGRP (83-132)-C-terminal Penetratin peptide (SEQ ID NO.: 81).

FIG. 89 is the primary sequence of an embodiment of the invention N-Terminal Penetratin-GLP-1 (7-37) (SEQ ID NO.: 82).

FIG. 90 is the primary sequence of an embodiment of the invention GLP-1 (7-37)—C-terminal Penetratin peptide (SEQ ID NO.: 83).

FIG. 91 is the primary sequence of an embodiment of the invention Exendin-4(3-39)-C-terminal Penetratin peptide (SEQ ID NO.: 84).

FIG. 92 is the primary sequence of an embodiment of the invention N-Terminal Penetratin-Exendin-4(3-39) (SEQ ID NO.: 85).

FIG. 93 is the primary sequence of an embodiment of the invention Extendin-3-C-terminal Penetratin peptide (SEQ ID NO.: 86).

FIG. 94 is the primary sequence of an embodiment of the invention Human C-peptide-Penetratin peptide (SEQ ID NO.: 87).

FIG. 95 is the primary sequence of an embodiment of the invention CGRP(8-37)—C-terminal Penetratin peptide (SEQ ID NO.: 88).

FIG. 96 is the primary sequence of an embodiment of the invention Human Aredomedullin (disulfide bridge Cys 16-Cys 21)-C-terminal Penetratin peptide (SEQ ID NO.: 89).

FIG. 97 is the primary sequence of an embodiment of the invention Human Aredomedullin (AM Pro-N-20 (PAMP-20)-C-terminal Penetratin peptide (SEQ ID NO.: 90).

FIG. 98 is the primary sequence of an embodiment of the invention PACAP38-C-terminal Penetratin peptide (SEQ ID NO.: 91).

FIG. 99 is the primary sequence of an embodiment of the invention PACAP27-C-terminal Penetratin peptide (SEQ ID NO.: 92).

FIG. 100 is the primary sequence of an embodiment of the invention Salmon Calcitonin (disulfide bridge Cys 1-Cys 7)-C-terminal Penetratin peptide (SEQ ID NO.: 93).

FIG. 101 is the primary sequence of an embodiment of the invention Salmon Calcitonin (8-32)-C-terminal Penetratin peptide (SEQ ID NO.: 94).

FIG. 102 is the primary sequence of an embodiment of the invention Human Neuromedin U-C-terminal Penetratin peptide (SEQ ID NO.: 95).

FIG. 103 is the primary sequence of an embodiment of the invention Porcine Neuromedin U-8-C-terminal Penetratin peptide (SEQ ID NO.: 96).

FIG. 104 is the primary sequence of an embodiment of the invention Rat Neuromedin-C-terminal Penetratin peptide (SEQ ID NO.: 97).

FIG. 105 is the primary sequence of an embodiment of the invention Octreotide-C-terminal Penetratin peptide (SEQ ID NO.: 98).

FIG. 106 is the primary sequence of an embodiment of the invention Octreotide, Tyr 3-Penetratin peptide (SEQ ID NO.: 99).

FIG. 107 is the primary sequence of an embodiment of the invention Coupling Factor 6 (CF6 Precursor (55-108)-Penetratin peptide (SEQ ID NO.: 100).

FIG. 108 is the primary sequence of an embodiment of the invention Coupling Factor 6 (CF6 Precursor (33-108)-Penetratin peptide (SEQ ID NO.: 101).

IV. DETAILED DESCRIPTION OF THE PREFERRED EMBODIMENTS

Figure 13:
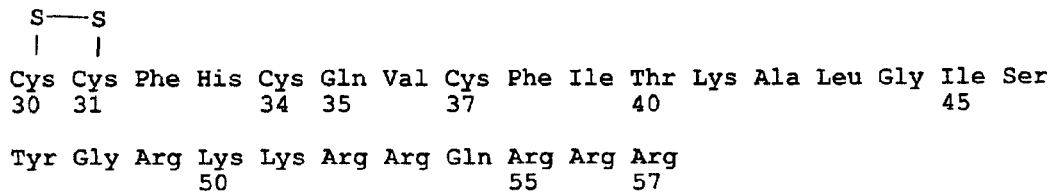

Cell permeable bioactive peptide conjugates having a first bioactive peptide region coupled to a second transport peptide region allowing transfer of the first bioactive peptide region and the second transport peptide region across biological membranes to enter intact living cells for regulation of biological responses.

First referring primarily to FIGS. 1 and 2, the transport peptide region of the invention can include either of the "Tat" transduction peptide (RKKRRQRRR) HIV 1 49-57 (SEQ ID NO. 102) (see FIG. 1) or the Penetratin peptide (RQIKIWFQNRRMKWKK) (SEQ ID NO. 103) (see FIG. 2). The transport peptide region can be coupled to each one the bioactive peptide regions further discussed below to produce inventive peptide conjugates which can transport across biological membranes into the living cell to regulate the corresponding biological responses.

Now referring primarily to FIGS. 3-7, which provides a non-limiting example of the a chemical synthesis method by which each transport peptide region and each bioactive peptide region and the corresponding bioactive peptide conjugates set forth by SEQ ID NOS.: 1-101) can be chemically synthesized by a solid phase peptide synthesis method using BOC-AA-resin as the solid support (as to the example shown by FIGS. 3-7 BOC-Glu(OcHex)-resin 0.6 mM/g, 0.67 g total 0.2 mM) and by addition of fluorenyloxymethylcarbonyl (FMOC) amino acids or tertbutyloxymethylcarbonyl (BOC) amino acids with either an automated peptide synthesizer or manually using FMOC or BOC synthesis techniques.

Naturally, other peptide synthesis strategies can be used to generate the polypeptides described herein and any specific synthesis strategy described herein is intended to allow the person of ordinary skill in the art to make and use the various embodiments of the cell permeable bioactive peptides encompassed by the invention and any particular synthesis described is not intended to be limiting with regard to alternate methods of making and using the various embodiments of the invention. See also, "Solid Phase Peptide Synthesis: A Practical Approach", E. Atherton and R. C. Sheppard, IRL Press, Oxford, England, hereby incorporated by reference.

FIGS. 3-7 specifically provides an illustrative example of a solid phase synthesis scheme for the synthesis of residues 30-86 of HIV-Tat (HIV-1 30-86) (SEQ ID NO. 104) (see FIG. 3) which provides differentially protected cysteine residues, S-acetamidomethyl-L-cysteine (Cys-Acm) to be incorporated at residue 30 and at residue 34 and S-Trt-L-cysteine to be incorporated at residue 31 and at residue 37 during chemical synthesis when an FMOC synthesis strategy is employed for the addition of cysteine amino acid residues, as shown by FIG. 4 (SEQ ID NO. 105) (this same strategy can be employed to synthesis any one of the inventive cell permeable bioactive peptides). Hydrogen fluoride cleavage of the protected HIV-1 30-86-resin including these S-protected cysteine residues yields a crude HIV-1 30-86 with S-acetamidomethyl-L-cysteine (Cys-Acm) residues at positions 30 and 34 and Cys-SH residues at positions 31 and 37 (SEQ ID NO. 106), as shown by FIG. 5.

The resulting mixture of polypeptides from the chemical synthesis of HIV-1 30-86 (or the resulting mixture of polypeptides from the chemical synthesis of any one of the cell permeable bioactive peptide conjugates described herein) can be separated from one another by reverse phase HPLC using columns packed with silica having a pore of between 80Å and 300Å and a C-4, C-8, or C-18 ligand attached. The columns can be equilibrated with 0.1% trifluoroacetic acid in water at a flow rate dependent on column size as would be understood by those of ordinary skill in the art. The synthetic peptide mixtures can be applied to the reverse phase HPLC columns and eluted with 0.1% trifluoroacetic acid in acetonitrile using a gradient of 0% to about 80% over a period of about 30 minutes to about 1 hour. Fractions can be collected at about 0.5 minute intervals. Fractions can be subsequently analyzed for homogeneity by re-application and elution from the reverse phase HPLC system, mass spectrometry, SDS-PAGE, or automated Edman degradation on an Applied Biosystems Model 470A protein sequencer. As described by Applied Biosystems, Inc., Foster City, Calif.

Purification by HPLC as above-described can result in an amount of HIV-1 30-86 Cys-Acm 30 and 34 (SEQ ID NO. 106) peptide as shown by FIG. 5 of sufficient quantity (about 16 milligrams with respect to the above-described synthesis and purification) and purity to be introduced into assays as described below or further treated with $I_2$/HOAc to form a disulfide bridge between Cys 31 and Cys 37 (Cys 31-Cys 37) (SEQ ID NO. 15), as shown by FIG. 6. Again purification of the $I_2$/HOAc treated peptide by HPLC, as above-described, can result in an amount of HIV-1 30-86 Cys-Acm 30 and Cys-Acm 34 and Cys 31-Cys 37 (SEQ ID NO. 15) which can be introduced into assays as described below or can be further treated with iodine in HOAc (7.5 mL and 25 mL respectively) to form a second disulfide bridge between Cys 30 and Cys 34 resulting in HIV-1 30-86 Cys 30-Cys 34 and Cys 31-Cys 37

(SEQ ID NO. 13) as shown by FIG. 7. HIV-1 30-86 Cys 30-Cys 34 and Cys 31-Cys 37 (SEQ ID NO. 13) can again be HPLC purified as above-described to yield a purified HIV-1 30-86 Cys 30-Cys 34 and Cys 31-Cys 37 (SEQ ID NO. 13) (about 3.05 mg in the above-described synthesis and purification) which presents a single significant peak on chromatograms when analyzed utilizing analytical HPLC and generates a single molecular ion at 6506.1 (M. W. 6505.42). Reduction of the disulfide bridges at Cys 30-Cys 34 and Cys 31-Cys 37, or other disulfide bridges with a reductant such as dithiothreitol, can result in the linear free sulfydryl peptide such as HIV 1-30-86 peptide (SEQ ID NO. 104) as shown by FIG. 3.

Now referring primarily to FIGS. 8-12, smaller linear HIV1 peptides such as HIV1-30-57 (SEQ. ID. NO.: 1) as shown by FIG. 8; HIV1-31-57 (SEQ ID. NO.: 2) as shown by FIG. 9; HIV1-32-57 (SEQ ID. NO.: 3) as shown by FIG. 10; HIV1-33-57 (SEQ ID. NO.: 4) as shown by FIG. 11; and HIV1-34-57 (SEQ ID. NO.: 5) as shown by FIG. 12 can be chemically synthesized in similar fashion as above-described. Each of these HIV1 peptides provide a first bioactive peptide region as a bioactive N-terminal region and further provide the "Tat" transduction peptide (RKKRRQRRR) (SEQ ID NO. 102) as a C-terminal transport region. Each of these HIV1 peptides transfer across the biological membrane to enter intact living cells and can regulate biological responses as further discussed.

Figure 14:
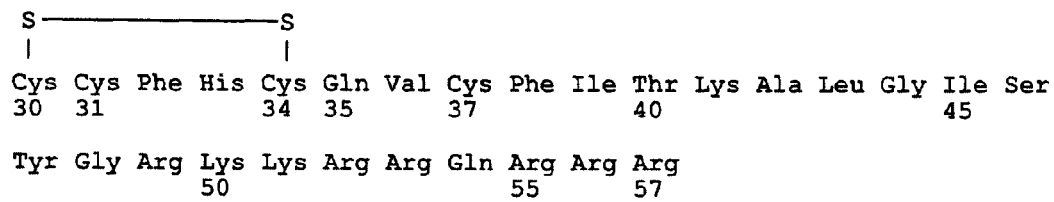
Figure 15:
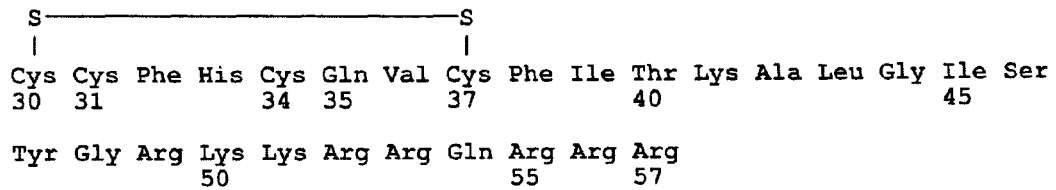
Figure 16:
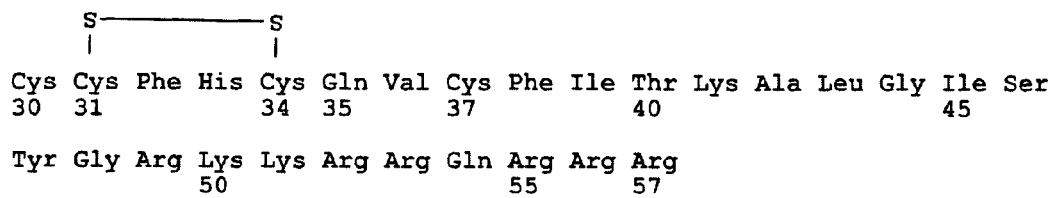
Figure 17:
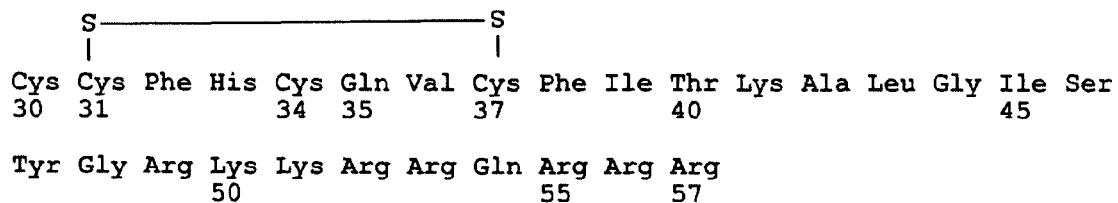
Figure 18:
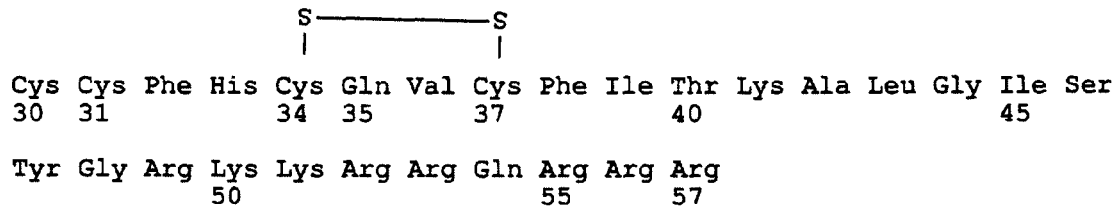
Figure 19:
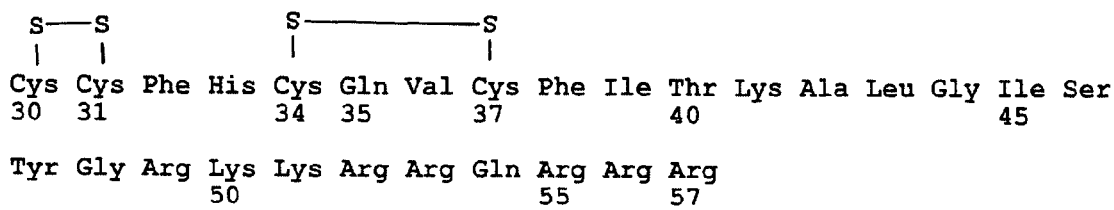
Figure 20:
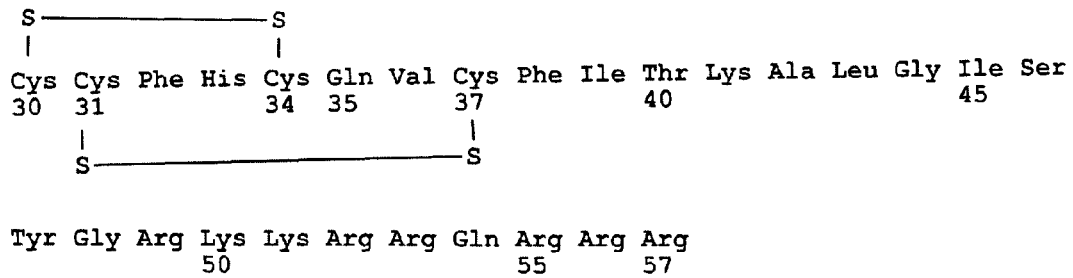
Figure 21:
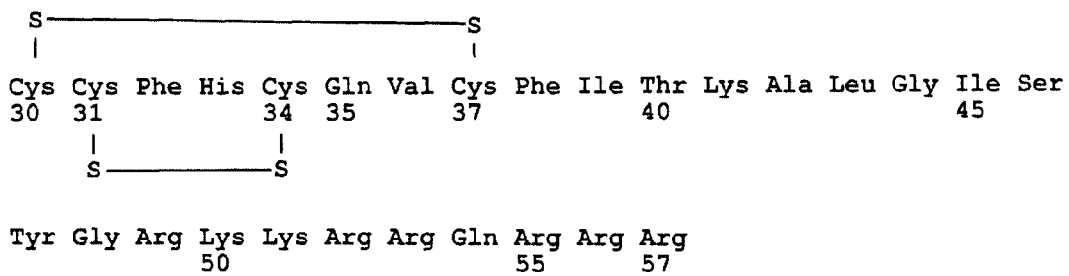
Figure 22:
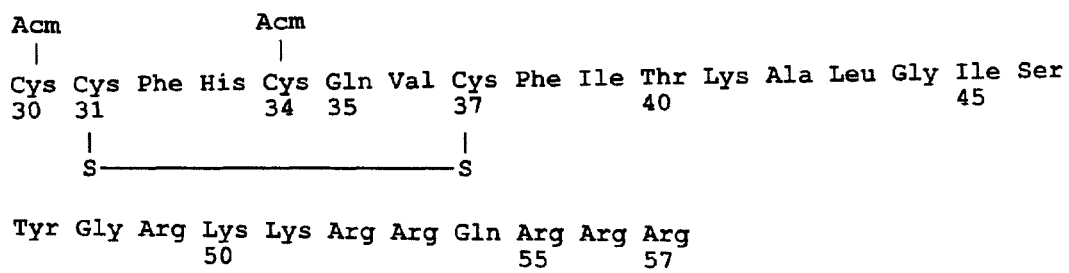
Figure 44:
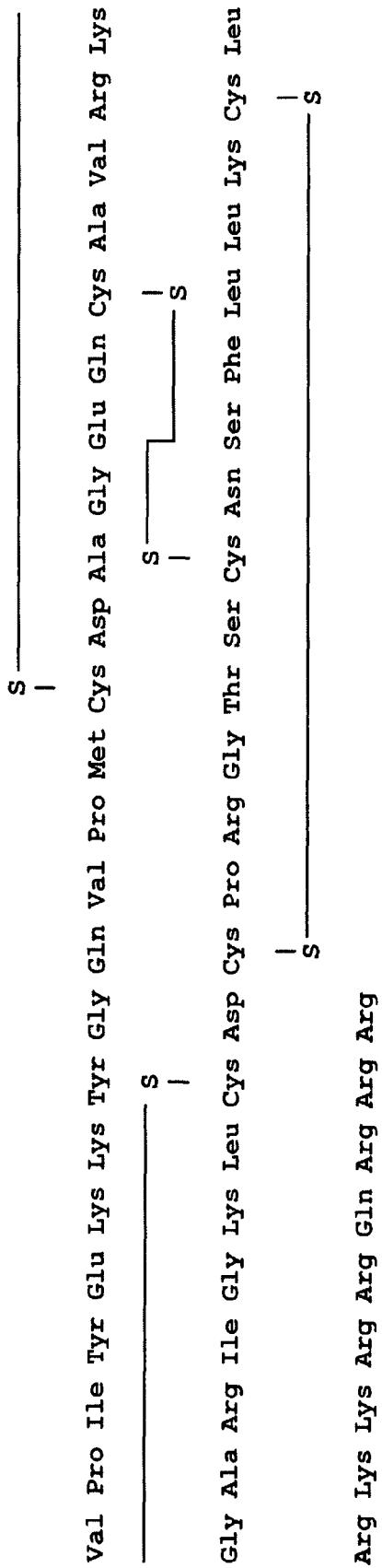
FIG. 44 is the primary sequence of an embodiment of the invention Human CART (55-102) C-terminal Tat peptide (SEQ ID NO.: 37).
Figure 87:
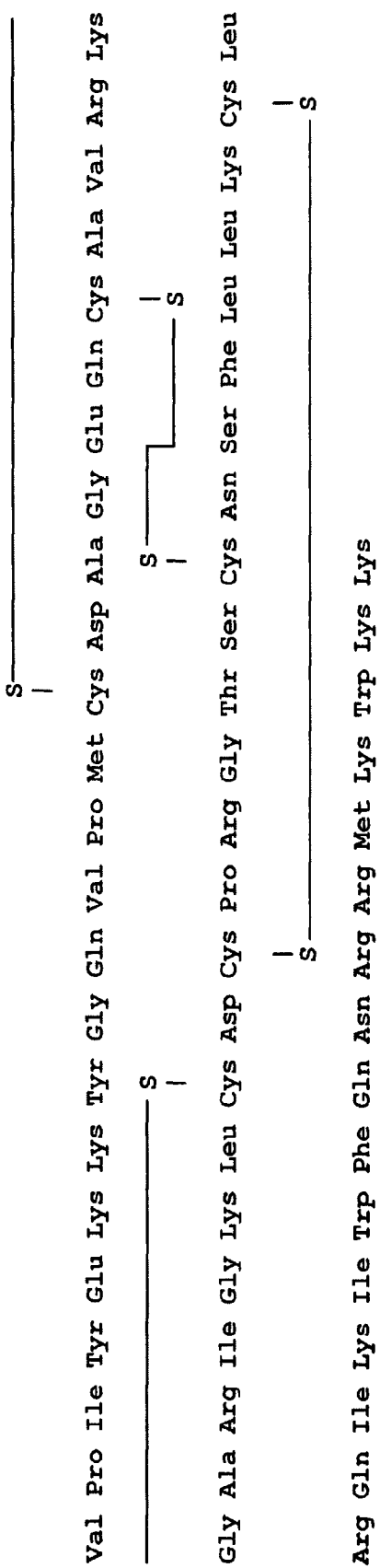
FIG. 87 is the primary sequence of an embodiment of the invention Human CART (disulfide bridges Cys 14-Cys 32; Cys 20-Cys 40; and Cys 34-Cys 47)-C-terminal Penetratin peptide (SEQ ID NO.: 80).

Now referring primarily to FIGS. 13-22, S-acetamidom-ethyl-L-cysteine (Cys-Acm) and S-Trt-L-cysteine can be incorporated in various combinations and permutations of residue 30, residue 31, residue 34 and residue 37 to generate isomeric peptides of HIV 1 30-57 (SEQ ID. NO.: 1) including one or more disulfide bridges of to produce HIV1 30-57 (Cys30-Cys31) (SEQ ID NO.: 6) as shown by FIG. 13; HIV1 30-57 (Cys30-Cys34) (SEQ ID NO.: 7) as shown by FIG. 14; HIV1 30-57 (Cys30-Cys37) (SEQ ID. NO.: 8) as shown by FIG. 15; HIV1 30-57 (Cys31-Cys34) (SEQ ID NO.: 9) as shown by FIG. 16; HIV1 30-57 (Cys31-Cys37) (SEQ ID NO.: 10) as shown by FIG. 17; HIV1 30-57 (Cys34-Cys37) (SEQ ID NO.: 11) as shown by FIG. 18; HIV1 30-57 (Cys30-Cys31)(Cys 34-Cys37) (SEQ ID NO.: 12) as shown by FIG. 19; HIV1 30-57 (Cys30-Cys34)(Cys 31-Cys37) (SEQ ID NO.: 13) as shown by FIG. 20; HIV1 30-57 (Cys30-Cys37) (Cys 31-Cys34) (SEQ ID NO.: 14) as shown by FIG. 21; HIV1 30-57 (Cys31-Cys37)(Cys 31-ACM)(Cys34-ACM) (SEQ ID NO.: 15) as shown by FIG. 22, each providing the "Tat" transduction peptide (RKKRRQRRR) (SEQ ID NO. 102) as a C-terminal transport region. Each of these HIV1 peptides transfer across the biological membrane to enter intact living cells and can regulate biological responses as further discussed.

Now referring to Table 1 other peptide fragments of the C-terminal region of the HIV1 30-86 peptide (SEQ ID NO. 106) (shown in FIG. 5) including as a non-limiting examples HIV1 41-60 (SEQ ID NO. 111); HIV1 48-84 (SEQ ID NO. 107); HIV1 58-86 (SEQ ID NO. 108); HIV1 62-86 (SEQ ID NO. 109); and HIV1 61-80 (SEQ ID NO. 110 and the peptide fragments of the C-terminal of the HIV1 30-57 (SEQ ID NO. 1) peptide including as a non-limiting example the HIV1 49-57 (SEQ ID NO. 102) Tat Region as shown by Figure can each be chemically synthesized an purified as above-described.

The invention also encompasses additional polypeptides or peptide fragments of HIV1 polypeptide sequences listed or as above-described which have substantially similar amino acid sequence as to the biologically active region HIV1 30-48; HIV1 31-48; HIV1 32-48; HIV 33-48; HIV 34-48 and which are capable of transfer into the cell by including a transport peptide region such as the "Tat" transduction peptide (RKKRRQRRR) HIV 1 49-57 (SEQ ID NO. 102) (see FIG. 1), or by replacement of the "Tat" transduction peptide with the Penetratin peptide (RQIKIWFQNRRMKWKK) (SEQ ID NO. 103) (see FIG. 2), or a poly-Arginine peptide (such as RRRRRRRRR) (SEQ ID NO. 112).

As to the HIV1 polypeptides above described and other peptides conjugates in the sequence listing, silent substitutions of amino acid residues wherein the replacement of the residue with structurally or chemically similar residue(s) which do not significantly alter the structure, conformation, or activity of the polypeptide are intended to fall within the scope of the claims of this application including without limitation silent substitutions of amino acids of the purified polypeptides described above or set out in the Sequence Listing and further including instances in which one or more residues has been removed from either end or both ends, or from an internal region of the peptides (for example without limitation removal of one or more residues between position 41 and position 48 of the HIV1 32-57 peptide), or wherein one or more residues is added to either end or both ends, or to an internal location in either peptide (for example without limitation insertion of one or more residues between position 41 and position 48 of the HIV1 30-57 peptide or HIV1 32-57 peptide). Additionally, purified polypeptides having chemical moieties or residues added for chemical or radiolabeling, such as, an added tyrosine for $^{125}$iodine labeling are also understood to be encompassed by the invention. Similarly, the N-terminus of purified polypeptide encompassed by the invention can be prepared as amino, acetyl, formyl, or left with a residual FMOC or BOC group intact. As to certain other embodiments of the invention, the C-terminus was left bound to the resin, or cleaved to yield various C-terminal moieties, such as carboxyl or amide by choice of the corresponding BHA, PAM, or amide solid phase resin.

Similarly, as to the specific peptide sequences included in the sequence listing, or as described above, each peptide or peptide analog is intended to be included within the description of this application. Moreover, with respect to those specific peptides which contain a single cysteine residue or a plurality of cysteine residues in the linear sequence, the numerous and wide variety of molecular structures capable of being generated by forming one or a plurality of disulfide bridge within a single peptide or between a plurality of peptides is also intended to be encompassed by this description.

Importantly, because certain peptide fragments of the HIV 1 Tat polypeptides encompassed by the invention have between one and four cysteine residues in their respective amino acid sequence these peptide fragments can be useful in generating numerous and varied peptide analogs which contain disulfide bridges as above-described or otherwise. Peptide fragments of the HIV 1 Tat polypeptides encompassed by the invention which contain certain disulfide bridges or combinations of disulfide bridges unexpectedly demonstrate similar or altered biological activity compared to the intact HIV 1 Tat polypeptides. As described below, the biological activity exhibited by the various peptide fragments of HIV 1 polypeptides, peptide fragments of HIV 1 polypeptides chemically synthesized, or peptide analogs thereof, can be greater or lesser than the intact HIV 1 Tat polypeptides and as such, the invention affords peptide fragments of HIV 1 Tat polypeptides which afford a graded range of biological activity.

To demonstrate biological activity of peptide fragments of HIV 1 polypeptides, peptide fragments of HIV 1 polypeptides chemically synthesized, or peptide analogs thereof, the mobilization of intracellular $Ca^{2+}$ can be measured. Neurons can be isolated from cerebral cortex according to the protocols for postnatal dissociated nuerons as disclosed for example by Huettner, J. E. and Baughman, R. W., *Primary Culture of Identified Neurons From the Visual Cortex of Postnatal Rats*, Journal of Neurosciences 6; 3044-3060 (1986); Brewer, G. J., *Isolation and Culture of Adult Rat Hippocampal Neurons*, Journal of Neuroscience Methods, 71:143-155 (1997); and Brailoiu et al., *NAADP Potentiates Neurite Outgrowth*, Journal of Biological Chemistry (in press), each hereby incorporated by reference. Newborn Sprague-Dawley rates (about 1 day to about 4 days old) were killed by cervical dislocation. Cerebral cortex was removed and quickly immersed in ice-cold phosphate buffer solution. After removal of meninges, tissue was minced into about I-millimeter blocks, incubated for about 45 minutes at 37° C. in Hanks balanced salt solution without $Ca^{2+}$ and $Mg^{2+}$ (Invitrogen, 1600 Faraday Avenue, Carlsbad, Calif. 92008) and supplemented with about 200 ug/mL penicillin, 0.1% EDTA and papain 0.15 mg/mL (Sigma-Aldrich, St. Louis, Mo.). In accordance with the procedure disclosed by Brewer, the tissue can be further dissociated by gentle mechanical trituration. After centrifugation at 500×g, cells can be re-suspended in fetal serum free media containing Neurobasal-ATM medium supplemented with 20 mM glutamine, 100 unites penicillin, 100 ug streptomycin, and B27 supplement all of which can be obtained for example from Invitrogen. The resulting cells can be plated at a low density of about $10^4$ on round glass coverslips in twenty four well plates. Neurons were cultured at 37° C. in 95% oxygen and 5% carbon dioxide for about 3 days to about 5 days. The mitotic inhibitor, cytosine P-arabino furanosidde (about 1 µM) which can be obtained from Sigma-Aldrich can be added to cultured neurons to inhibit glial cell proliferation according to the procedure disclosed by Billingsley, M. L. and Mandel, H. G., *Effects of DNA Synthesis Inhibitors on Post-Traumatic Glial Cell Proliferation*, Journal of Pharmacology and Experimental Therapeutics, 222: 765-770 (1982).

Measurement of mobilized intracellular calcium ion ($Ca^{2+}$) in dissociate cultured neurons in response to peptide fragments of HIV-1 Tat polypeptides can be performed as disclosed by Brailoiu E. et al. Neurons cultured about 24 hours on coverslips as above-described were loaded in HBBS with 5µ Fura-2 AM dye at room temperature (about 20° C.) for about 45 minutes in the dark, then washed three times with Fura-2 AM free buffer and allowed to incubate to allow de-esterification of the dye for about 45 minutes. Under these conditions, compartmentalization of the dye was minimal (about 9.2%±0.2% n=6) as judged from the ratio of fluorescence signals after selective permeabilization of the plasma membrane (10 µM β-escein) and full permeabilization of the cultured cells (60 µg/mL saponin). The coverslips were mounted in a custom designed bath on the stage of a S300 Axiovert Nikon inverted microscope equipped with a C&L Instruments fluorimeter as described by Brailoiu et al. The Fura-2 fluorescent signal was calibrated by successive addition of 20 µg/mL digitonin, 20 mM EDTA, and 0.5 mM $MnCl_2$. $Ca^{2+}$ values were then obtained using the procedures and equation described by Grynkiewicz, G., Poenie, M., and Tsien, R. Y. *A New Generation of $Ca^{2+}$ Indicators With Greatly Improved Fluorescence Properties*, J. Biol. Chem., 260:3440-3450 (1989)

Now referring to Table 1, measurement of intracellular calcium ion (Ca 2+) in dissociate cultured neurons shows that $Ca^{2+}$ can be mobilized in response to peptide fragments of HIV-1 Tat polypeptides and analogs thereof. Table 1. Effect of HIV1-Tat Polypeptides on $[Ca^{2+}]$ Response in Dissociate and Cultured Cortical Neurons

TABLE 1

Effect of HIV1-Tat Polypeptides on $[Ca^{2+}]$ Response in Dissociate and Cultured Cortical Neurons

| HIV1 Tat Polypeptide | SEQ NO. | $[Ca^{2+}]$ nM | n |
|---|---|---|---|
| 30-47 (Cys 30-Cys34)(Cys 31-Cys37) | 113 | No Response | 6 |
| 30-57 Cys30Acm, Cys34Acm, (Cys31-Cys37) | 15 | 197 ± 35 | 10 |
| 30-57 (Cys30-Cys34)(Cys31-Cys37) | 13 | 528 ± 60 | 10 |
| 30-57 (Cys30-Cys31)(Cys34-Cys37) | 12 | 258 ± 54 | 10 |
| 30-57 (Cys30-Cys37)(Cys31-Cys34) | 8 | 197 ± 46 | 10 |
| 30-86 (Cys30-Cys34)(Cys31-Cys37) | 114 | 390 ± 21 | 9 |
| 32-62 (Cys34-Cys37) | 115 | 752 ± 59 | 8 |
| 41-60 | 111 | 66 ± 13 | 6 |
| 48-84 | 107 | 80 ± 28 | 7 |
| 49-57 | 102 | No Response | 8 |
| 58-86 | 108 | 54 ± 28 | 7 |
| 61-80 | 110 | 56 ± 20 | 6 |
| 62-86 | 109 | No Response | 5 |

Now referring primarily to Table 1 and FIGS. 7-22, it can be understood that HIV1 30-57 (Cys30-Cys34)(Cys31-Cys37) (SEQ ID.: 13) which further includes a second transport peptide region can transfer across biological membranes to enter intact living cells for regulation of biological responses which includes for the HIV 1 molecule the mobilization of intracellular calcium ion ($Ca^{2+}$). By comparison, the that HIV1 30-47 (Cys30-Cys34)(Cys31-Cys37) (SEQ ID NO. 113) which lacks the second transport peptide region does not enter intact living cells and cannot mobilize intracellular calcium ion. Understandably the second peptide region of the invention can comprise the Tat transduction domain (RKKRRQRRR) (SEQ ID NO. 102) HIV 1 49-57 as shown by FIG. 1, which allows transfer of the first portion bioactive peptide region into the cell; however, it is not intended that the second peptide region of the invention be limited solely to the use of Tat transduction domain HIV 49-57 (SEQ ID NO. 102) for transfer of the first portion of the peptide across the cell membrane, and it is now understood that Penetratin (SEQ ID NO. 103) as shown by FIG. 2 can also allow the transfer of the first region of HIV1 peptides and analogs across cell membranes to the target binding site.

Also, it is now understood that the second transfer peptide region in the form of the Tat transduction domain (RKKRRQRRR) (SEQ ID NO. 102) HIV 1 49-57 as shown by FIG. 1 or in the form of the Penetratin (SEQ ID NO. 103) as shown by FIG. 2 can allow the transfer of a wide variety of peptide fragments, polypeptides, even when the first bioactive peptide region has a lesser level of biological activity or a greater level of biological activity. Accordingly, the second transfer region in the form of the Tat transduction domain (RKKRRQRRR) (SEQ ID NO. 102) HIV 1 49-57 as shown by FIG. 1 or in the form of the Penetratin as shown by FIG. 2 can accomplish the transfer across biological membranes of any of the above-described peptide fragments, peptide fragment analogs, or peptide fragments or peptide fragment analogs of HIV 1. Specifically, the second peptide region in the form of the TAT transduction domain or the Penetrin peptide can transfer any one or a mixture of any of biologically active regions of SEQ ID NOS.: 1-15.

The invention can further encompass peptides which include a first peptide region coupled to a second peptide region which can function in the cell to regulate any one of mobilizing intracellular calcium ion including but not limited to calcium from the endoplasmic reticulum, tharsigargin-sensitive and tharsigargin-insensitives stores, acid filled calcium stores; activating calcium-induced calcium release; opening voltage-gated calcium channels; acting as HIV-1 tat antagonists; acting as calcium mobilization antagonists; treating vascular disorders, stroke, or hypertension; treating HIV-1 dementia, Alzheimer's Disease, or other dementia or neurological disorders; treating elevated or low calcium levels; the production of interferon and the subsequent cascade of events leading to inhibition of protein synthesis; binding of a variety of cellular factors, including, but not limited to HIV long terminal repeat (LTR) RNA trans-activation response (TAR) element region, ATPase and DNA helicase, 36-kDA nuclear factor, as well as the transcriptional factors FFIID and Sp11; along with affecting neurotransmitter release including, but not limited to, the release of acetylcholine and inducing neurological impairments and neurotoxicity by mechanisms involving $Ca^{2+}$ homeostasis after binding and depolarizing neuronal membranes, and specifically includes without limitation each of the peptide structures described by SEQ ID NO.: 8, SEQ ID NO.: 12, SEQ ID NO.: 13, SEQ ID NO.: 15, HIV1 36-62 (Cys 34-Cys 37), HIV1 30-86 (Cys30-Cys34)(Cys31-Cys37) (SEQ ID NO. 114) along with any analogs thereof, as above described.

Now referring to FIGS. 23-108, which describe the structure of additional cell permeable bioactive peptide conjugates encompassed by the invention, each of which can be synthesized as above-described utilizing the appropriate protected amino acid residue in each cycle of the solid phase synthesis and then purified and treated in a manner similar to that above-described to generate the linear or disulfide bridged cell permeable bioactive conjugates set out by SEQ. ID. NOS.: 16-101.

FIGS. 23-65 (SEQ ID NOS.: 16-58) describe a second transfer peptide region which comprises the Tat transduction domain (RKKRRQRRR) (SEQ ID NO. 102) HIV 1 49-57 (FIG. 1). The Tat transduction domain (RKKRRQRRR) (SEQ ID NO. 102) HIV 1 49-57 can when included at either the N-terminus or the C-terminus of the first biologically active peptide region as set out by SEQ ID NOS.: 8-50, and as shown by FIGS. 8-50, can allow transfer of the entirety of the synthetic peptide into the living cell, including the first bioactive peptide region of the synthetic peptide which can bind the target receptor as an antagonist or agonist of the corresponding biological activity.

FIGS. 66-108 (SEQ ID NOS.: 59-101) describe an alternate second transfer peptide region which comprises the Penetratin peptide (RQIKIWFQNRRMKWKK) (SEQ ID NO.: 103)(FIG. 2). The Penetratin peptide (RQIKIWFQNRRMKWKK) (SEQ ID NO.: 103) when included at either the N-terminus or the C-terminus of SEQ ID NOS.: 59-101, as shown by FIGS. 66-108, can allow transfer of the entirety of the synthetic peptide into the living cell, including the first bioactive peptide region of the synthetic peptide which can bind the target receptor as an antagonist or agonist of the biological activity above-described.

The biological activity of each of the synthetic peptide conjugates encompassed by the invention (SEQ ID NOS: 1-101) can be demonstrated by delivering the peptide conjugates by injection, tissue perfusion, or cell incubation, or aerosol, as above-described. The level of biological activity can be compared to the biological activity of the biologically active synthetic peptides conventionally assayed. As to each embodiment of the invention (SEQ ID NOS: 1-101) a level of such biological activity can be retained.

As can be easily understood from the foregoing, the basic concepts of the present invention may be embodied in a variety of ways. The invention involves numerous and varied embodiments of cell permeable bioactive peptide conjugates and methods of making and using such cell permeable bioactive peptide conjugates.

As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "conjugate" should be understood to encompass disclosure of the act of "conjugating"—whether explicitly discussed or not—and, conversely, were there effectively disclosure of the act of "conjugating", such a disclosure should be understood to encompass disclosure of a "conjugate" and even a "means for conjugating." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the cell permeable bioactive peptide conjugates herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incor-

I claim:

1. A purified polypeptide selected from the group consisting of: the polypeptide consisting of SEQ ID NO. 6, the polypeptide consisting of SEQ ID NO. 7, the polypeptide consisting of SEQ ID NO. 8, the polypeptide consisting of SEQ ID NO. 9, the polypeptide consisting of SEQ ID NO. 10, the polypeptide consisting of SEQ ID NO. 11, the polypeptide consisting of SEQ ID NO. 12, the polypeptide consisting of SEQ ID NO. 13, the polypeptide consisting of SEQ ID NO. 14, and the polypeptide consisting of SEQ ID NO. 15; and wherein, the polypeptide may optionally be acetylated at its N-terminus and/or amidated at its C-terminus; and wherein at least one amino acid residue in the polypeptide may be conservatively substituted with another amino acid residue.

2. The purified polypeptide of claim 1, wherein said purified polypeptide consists of SEQ ID NO. 6.

3. The purified polypeptide of claim 1, wherein said purified polypeptide consists of SEQ ID NO. 7.

4. The purified polypeptide of claim 1, wherein said purified polypeptide consists of SEQ ID NO. 8.

5. The purified polypeptide of claim 1, wherein said purified polypeptide consists of SEQ ID NO. 9.

6. The purified polypeptide of claim 1, wherein said purified polypeptide consists of SEQ ID NO. 10.

7. The purified polypeptide of claim 1, wherein said purified polypeptide consists of SEQ ID NO. 11.

8. The purified polypeptide of claim 1, wherein said purified polypeptide consists of SEQ ID NO. 12.

9. The purified polypeptide of claim 1, wherein said purified polypeptide consists of SEQ ID NO. 13.

10. The purified polypeptide of claim 1, wherein said purified polypeptide consists of SEQ ID NO. 14.

11. The purified polypeptide of claim 1, wherein said purified polypeptide consists of SEQ ID NO. 15.

* * * * *

SEQUENCE LISTING

<160> NUMBER OF SEQ ID NOS: 115

<210> SEQ ID NO 1
<211> LENGTH: 28
<212> TYPE: PRT
<213> ORGANISM: Human immunodeficiency virus type 1

<400> SEQUENCE: 1

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg
            20                  25

<210> SEQ ID NO 2
<211> LENGTH: 27
<212> TYPE: PRT
<213> ORGANISM: Human immunodeficiency virus type 1

<400> SEQUENCE: 2

Cys Phe His Cys Gln Val Cys Phe Ile Thr Lys Ala Leu Gly Ile Ser
1               5                   10                  15

Tyr Gly Arg Lys Lys Arg Arg Gln Arg Arg
            20                  25

<210> SEQ ID NO 3
<211> LENGTH: 26
<212> TYPE: PRT
<213> ORGANISM: Human immunodeficiency virus type 1

<400> SEQUENCE: 3

Phe His Cys Gln Val Cys Phe Ile Thr Lys Ala Leu Gly Ile Ser Tyr
1               5                   10                  15

Gly Arg Lys Lys Arg Arg Gln Arg Arg
            20                  25

<210> SEQ ID NO 4
<211> LENGTH: 25
<212> TYPE: PRT
<213> ORGANISM: Human immunodeficiency virus type 1

<400> SEQUENCE: 4

His Cys Gln Val Cys Phe Ile Thr Lys Ala Leu Gly Ile Ser Tyr Gly
1               5                   10                  15

Arg Lys Lys Arg Arg Gln Arg Arg
            20                  25

<210> SEQ ID NO 5
<211> LENGTH: 24
<212> TYPE: PRT
<213> ORGANISM: Human immunodeficiency virus type 1

<400> SEQUENCE: 5

Cys Gln Val Cys Phe Ile Thr Lys Ala Leu Gly Ile Ser Tyr Gly Arg
1               5                   10                  15

Lys Lys Arg Arg Gln Arg Arg
            20

<210> SEQ ID NO 6
<211> LENGTH: 28

```
<212> TYPE: PRT
<213> ORGANISM: Human immunodeficiency virus type 1
<220> FEATURE:
<221> NAME/KEY: DISULFID
<222> LOCATION: (1)..(2)

<400> SEQUENCE: 6

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
            20                  25

<210> SEQ ID NO 7
<211> LENGTH: 28
<212> TYPE: PRT
<213> ORGANISM: Human immunodeficiency virus type 1
<220> FEATURE:
<221> NAME/KEY: DISULFID
<222> LOCATION: (1)..(5)

<400> SEQUENCE: 7

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
            20                  25

<210> SEQ ID NO 8
<211> LENGTH: 28
<212> TYPE: PRT
<213> ORGANISM: Human immunodeficiency virus type 1
<220> FEATURE:
<221> NAME/KEY: DISULFID
<222> LOCATION: (1)..(8)

<400> SEQUENCE: 8

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
            20                  25

<210> SEQ ID NO 9
<211> LENGTH: 28
<212> TYPE: PRT
<213> ORGANISM: Human immunodeficiency virus type 1
<220> FEATURE:
<221> NAME/KEY: DISULFID
<222> LOCATION: (2)..(5)

<400> SEQUENCE: 9

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
            20                  25

<210> SEQ ID NO 10
<211> LENGTH: 28
<212> TYPE: PRT
<213> ORGANISM: Human immunodeficiency virus type 1
<220> FEATURE:
<221> NAME/KEY: DISULFID
<222> LOCATION: (2)..(8)

<400> SEQUENCE: 10

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
```

20                  25

<210> SEQ ID NO 11
<211> LENGTH: 28
<212> TYPE: PRT
<213> ORGANISM: Human immunodeficiency virus type 1
<220> FEATURE:
<221> NAME/KEY: DISULFID
<222> LOCATION: (5)..(8)

<400> SEQUENCE: 11

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
            20                  25

<210> SEQ ID NO 12
<211> LENGTH: 28
<212> TYPE: PRT
<213> ORGANISM: Human immunodeficiency virus type 1
<220> FEATURE:
<221> NAME/KEY: DISULFID
<222> LOCATION: (1)..(2)
<220> FEATURE:
<221> NAME/KEY: DISULFID
<222> LOCATION: (5)..(8)

<400> SEQUENCE: 12

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
            20                  25

<210> SEQ ID NO 13
<211> LENGTH: 28
<212> TYPE: PRT
<213> ORGANISM: Human immunodeficiency virus type 1
<220> FEATURE:
<221> NAME/KEY: DISULFID
<222> LOCATION: (1)..(5)
<220> FEATURE:
<221> NAME/KEY: DISULFID
<222> LOCATION: (2)..(8)

<400> SEQUENCE: 13

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
            20                  25

<210> SEQ ID NO 14
<211> LENGTH: 28
<212> TYPE: PRT
<213> ORGANISM: Human immunodeficiency virus type 1
<220> FEATURE:
<221> NAME/KEY: DISULFID
<222> LOCATION: (1)..(8)
<220> FEATURE:
<221> NAME/KEY: DISULFID
<222> LOCATION: (2)..(5)

<400> SEQUENCE: 14

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg
            20                  25

```
<210> SEQ ID NO 15
<211> LENGTH: 28
<212> TYPE: PRT
<213> ORGANISM: Human immunodeficiency virus type 1
<220> FEATURE:
<221> NAME/KEY: ACM
<222> LOCATION: (1)..(1)
<223> OTHER INFORMATION: cys-s-acetamidomethyl
<220> FEATURE:
<221> NAME/KEY: DISULFID
<222> LOCATION: (2)..(8)
<220> FEATURE:
<221> NAME/KEY: ACM
<222> LOCATION: (5)..(5)
<223> OTHER INFORMATION: cys-s-acetamidomethyl

<400> SEQUENCE: 15

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg
            20                  25

<210> SEQ ID NO 16
<211> LENGTH: 17
<212> TYPE: PRT
<213> ORGANISM: Artificial Sequence
<220> FEATURE:
<223> OTHER INFORMATION: chemically synthesized peptide
<220> FEATURE:
<221> NAME/KEY: ACETYL
<222> LOCATION: (1)..(1)
<223> OTHER INFORMATION: n-terminus acetyl

<400> SEQUENCE: 16

Lys Pro Ser Ser Pro Pro Glu Glu Arg Lys Lys Arg Arg Gln Arg Arg
1               5                   10                  15

Arg

<210> SEQ ID NO 17
<211> LENGTH: 33
<212> TYPE: PRT
<213> ORGANISM: Artificial Sequence
<220> FEATURE:
<223> OTHER INFORMATION: chemically synthesized peptide

<400> SEQUENCE: 17

Met Ala Pro Arg Gly Phe Ser Cys Leu Leu Leu Leu Thr Ser Glu Ile
1               5                   10                  15

Asp Leu Pro Val Lys Arg Arg Ala Arg Lys Lys Arg Arg Gln Arg Arg
            20                  25                  30

Arg

<210> SEQ ID NO 18
<211> LENGTH: 33
<212> TYPE: PRT
<213> ORGANISM: Artificial Sequence
<220> FEATURE:
<223> OTHER INFORMATION: chemically synthesized peptide

<400> SEQUENCE: 18

Arg Lys Lys Arg Arg Gln Arg Arg Met Ala Pro Arg Gly Phe Ser
1               5                   10                  15

Cys Leu Leu Leu Leu Thr Ser Glu Ile Asp Leu Pro Val Lys Arg Arg
            20                  25                  30

Ala
```

```
<210> SEQ ID NO 19
<211> LENGTH: 22
<212> TYPE: PRT
<213> ORGANISM: Artificial Sequence
<220> FEATURE:
<223> OTHER INFORMATION: chemically synthesized peptide
<220> FEATURE:
<221> NAME/KEY: P-GLU
<222> LOCATION: (1)..(1)
<223> OTHER INFORMATION: para-glutamic acid

<400> SEQUENCE: 19

Glu Arg Pro Arg Leu Ser His Lys Gly Pro Met Pro Phe Arg Lys Lys
1               5                   10                  15

Arg Arg Gln Arg Arg Arg
            20

<210> SEQ ID NO 20
<211> LENGTH: 45
<212> TYPE: PRT
<213> ORGANISM: Artificial Sequence
<220> FEATURE:
<223> OTHER INFORMATION: chemically synthesized peptide

<400> SEQUENCE: 20

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe Arg Lys Lys Arg Arg Gln Arg Arg
            35                  40              45

<210> SEQ ID NO 21
<211> LENGTH: 37
<212> TYPE: PRT
<213> ORGANISM: Artificial Sequence
<220> FEATURE:
<223> OTHER INFORMATION: chemically synthesized peptide
<220> FEATURE:
<221> NAME/KEY: SER-DES-OCTANOYL
<222> LOCATION: (3)..(3)
<223> OTHER INFORMATION: serine-des-octanoyl

<400> SEQUENCE: 21

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg Arg Lys Lys Arg
            20                  25                  30

Arg Gln Arg Arg Arg
            35

<210> SEQ ID NO 22
<211> LENGTH: 37
<212> TYPE: PRT
<213> ORGANISM: Artificial Sequence
<220> FEATURE:
<223> OTHER INFORMATION: chemically synthesized peptide
<220> FEATURE:
<221> NAME/KEY: SERINE-OCTANOYL
<222> LOCATION: (3)..(3)
<223> OTHER INFORMATION: serine-octanoyl

<400> SEQUENCE: 22

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg Arg Lys Lys Arg
            20                  25                  30
```

```
Arg Gln Arg Arg Arg
        35

<210> SEQ ID NO 23
<211> LENGTH: 37
<212> TYPE: PRT
<213> ORGANISM: Artificial Sequence
<220> FEATURE:
<223> OTHER INFORMATION: chemically synthesized peptide
<220> FEATURE:
<221> NAME/KEY: SER-OCTANOYL
<222> LOCATION: (3)..(3)
<223> OTHER INFORMATION: serine-octanoyl

<400> SEQUENCE: 23

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg Arg Lys Lys Arg
            20                  25                  30

Arg Gln Arg Arg Arg
        35

<210> SEQ ID NO 24
<211> LENGTH: 17
<212> TYPE: PRT
<213> ORGANISM: Artificial Sequence
<220> FEATURE:
<223> OTHER INFORMATION: chemically synthesized peptide

<400> SEQUENCE: 24

Asp Arg Val Tyr Ile His Pro Phe Arg Lys Lys Arg Gln Arg Arg
1               5                   10                  15

Arg

<210> SEQ ID NO 25
<211> LENGTH: 16
<212> TYPE: PRT
<213> ORGANISM: Artificial Sequence
<220> FEATURE:
<223> OTHER INFORMATION: chemically synthesized peptide

<400> SEQUENCE: 25

Asp Arg Val Tyr Ile His Pro Arg Lys Lys Arg Gln Arg Arg Arg
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: chemically synthesized peptide

<400> SEQUENCE: 26

Val Tyr Ile His Pro Phe Arg Lys Lys Arg Gln Arg Arg Arg
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: chemically synthesized peptide
<220> FEATURE:
<221> NAME/KEY: D-TRP
<222> LOCATION: (2)..(2)
<223> OTHER INFORMATION: d-tryptophan
<220> FEATURE:
```

```
<221> NAME/KEY: D-PHE
<222> LOCATION: (5)..(5)
<223> OTHER INFORMATION: d-phenylalanine

<400> SEQUENCE: 27

His Trp Lys Trp Phe Lys Arg Lys Lys Arg Arg Gln Arg Arg Arg
1               5                   10                  15

<210> SEQ ID NO 28
<211> LENGTH: 43
<212> TYPE: PRT
<213> ORGANISM: Artificial Sequence
<220> FEATURE:
<223> OTHER INFORMATION: chemically synthesized peptide

<400> SEQUENCE: 28

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr Arg Lys Lys Arg Arg Gln Arg Arg
        35                  40

<210> SEQ ID NO 29
<211> LENGTH: 43
<212> TYPE: PRT
<213> ORGANISM: Artificial Sequence
<220> FEATURE:
<223> OTHER INFORMATION: chemically synthesized peptide

<400> SEQUENCE: 29

Arg Lys Lys Arg Arg Gln Arg Arg Ile Lys Pro Glu Ala Pro Gly
1               5                   10                  15

Glu Asp Ala Ser Pro Glu Glu Leu Asn Arg Tyr Tyr Ala Ser Leu Arg
            20                  25                  30

His Tyr Leu Asn Leu Val Thr Arg Gln Arg Tyr
        35                  40

<210> SEQ ID NO 30
<211> LENGTH: 22
<212> TYPE: PRT
<213> ORGANISM: Artificial Sequence
<220> FEATURE:
<223> OTHER INFORMATION: chemically synthesized peptide
<220> FEATURE:
<221> NAME/KEY: ACETYL
<222> LOCATION: (1)..(1)
<223> OTHER INFORMATION: n-terminus acetyl

<400> SEQUENCE: 30

Ser Tyr Ser Met Glu His Phe Arg Trp Gly Lys Pro Val Arg Lys Lys
1               5                   10                  15

Arg Arg Gln Arg Arg Arg
            20

<210> SEQ ID NO 31
<211> LENGTH: 28
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (7)..(16)

<400> SEQUENCE: 31
```

```
Asp Phe Asp Met Leu Arg Cys Met Leu Gly Arg Val Tyr Arg Pro Cys
1               5                   10                  15

Trp Gln Val Arg Lys Arg Arg Gln Arg Arg Arg
            20                  25
```

```
<210> SEQ ID NO 32
<211> LENGTH: 23
<212> TYPE: PRT
<213> ORGANISM: Artificial Sequence
<220> FEATURE:
<223> OTHER INFORMATION: chemically synthesized peptide
<220> FEATURE:
<221> NAME/KEY: P-GLU
<222> LOCATION: (1)..(1)
<223> OTHER INFORMATION: para-glutamic acid

<400> SEQUENCE: 32

Glu Gln Arg Leu Gly Asn Gln Trp Ala Val Gly His Leu Met Arg Lys
1               5                   10                  15

Lys Arg Arg Gln Arg Arg Arg
            20
```

```
<210> SEQ ID NO 33
<211> LENGTH: 60
<212> TYPE: PRT
<213> ORGANISM: Artificial Sequence
<220> FEATURE:
<223> OTHER INFORMATION: chemically synthesized peptide

<400> SEQUENCE: 33

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Pro Lys Thr Arg Lys Lys Arg Arg Gln Arg Arg Arg
    50                  55                  60
```

```
<210> SEQ ID NO 34
<211> LENGTH: 37
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (7)..(23)

<400> SEQUENCE: 34

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Lys Lys Arg
            20                  25                  30

Arg Gln Arg Arg Arg
        35
```

```
<210> SEQ ID NO 35
<211> LENGTH: 41
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (10)..(26)
```

<400> SEQUENCE: 35

Ser Pro Lys Met Val Gln Arg Ser Gly Cys Phe Gly Arg Lys Met Asp
1               5                   10                  15

Arg Ile Ser Ser Ser Gly Leu Gly Cys Lys Val Leu Arg Arg His
            20                  25                  30

Arg Lys Lys Arg Arg Gln Arg Arg
        35                  40

<210> SEQ ID NO 36
<211> LENGTH: 41
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (10)..(26)

<400> SEQUENCE: 36

Asn Ser Lys Met Ala His Ser Ser Cys Phe Gly Gln Lys Ile Asp
1               5                   10                  15

Arg Ile Gly Ala Val Ser Arg Leu Gly Cys Asp Gly Leu Arg Leu Phe
            20                  25                  30

Arg Lys Lys Arg Arg Gln Arg Arg
        35                  40

<210> SEQ ID NO 37
<211> LENGTH: 57
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (14)..(32)
<220> FEATURE:
<221> NAME/KEY: DISULFID
<222> LOCATION: (20)..(40)
<220> FEATURE:
<221> NAME/KEY: DISULFID
<222> LOCATION: (34)..(47)

<400> SEQUENCE: 37

Val Pro Ile Tyr Glu Lys Lys Tyr Gly Gln Val Pro Met Cys Asp Ala
1               5                   10                  15

Gly Glu Gln Cys Ala Val Arg Lys Gly Ala Arg Ile Gly Lys Leu Cys
            20                  25                  30

Asp Cys Pro Arg Gly Thr Ser Cys Asn Ser Phe Leu Leu Lys Cys Leu
        35                  40                  45

Arg Lys Lys Arg Arg Gln Arg Arg
    50                  55

<210> SEQ ID NO 38
<211> LENGTH: 59
<212> TYPE: PRT
<213> ORGANISM: Artificial Sequence
<220> FEATURE:
<223> OTHER INFORMATION: chemically synthesized peptide

<400> SEQUENCE: 38

Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
            20                  25                  30

```
Ala Phe Cys Tyr Cys Arg Lys Leu Gly Thr Ala Met Asn Pro Cys Ser
        35                  40                  45

Arg Thr Arg Lys Lys Arg Gln Arg Arg
        50                  55

<210> SEQ ID NO 39
<211> LENGTH: 40
<212> TYPE: PRT
<213> ORGANISM: Artificial Sequence
<220> FEATURE:
<223> OTHER INFORMATION: chemically synthesized peptide

<400> SEQUENCE: 39

Arg Lys Lys Arg Arg Gln Arg Arg His Ala Glu Gly Thr Phe Thr
1               5                   10                  15

Ser Asp Val Ser Ser Tyr Leu Glu Gly Gln Ala Ala Lys Glu Phe Ile
            20                  25                  30

Ala Trp Leu Val Lys Gly Arg Gly
        35                  40

<210> SEQ ID NO 40
<211> LENGTH: 40
<212> TYPE: PRT
<213> ORGANISM: Artificial Sequence
<220> FEATURE:
<223> OTHER INFORMATION: chemically synthesized peptide

<400> SEQUENCE: 40

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Lys Lys Arg Arg Gln Arg Arg
        35                  40

<210> SEQ ID NO 41
<211> LENGTH: 46
<212> TYPE: PRT
<213> ORGANISM: Artificial Sequence
<220> FEATURE:
<223> OTHER INFORMATION: chemically synthesized peptide

<400> SEQUENCE: 41

Glu Gly Thr Phe Thr Ser Asp Leu Ser Lys Gln Met Glu Glu Glu Ala
1               5                   10                  15

Val Arg Leu Phe Ile Glu Trp Leu Lys Asn Gly Gly Pro Ser Ser Gly
            20                  25                  30

Ala Pro Pro Pro Ser Arg Lys Lys Arg Arg Gln Arg Arg
        35                  40                  45

<210> SEQ ID NO 42
<211> LENGTH: 46
<212> TYPE: PRT
<213> ORGANISM: Artificial Sequence
<220> FEATURE:
<223> OTHER INFORMATION: chemically synthesized peptide
<220> FEATURE:
<221> NAME/KEY: AMIDE
<222> LOCATION: (46)..(46)
<223> OTHER INFORMATION: c-terminus amide

<400> SEQUENCE: 42

Arg Lys Lys Arg Arg Gln Arg Arg Glu Gly Thr Phe Thr Ser Asp
1               5                   10                  15
```

```
Leu Ser Lys Gln Met Glu Glu Ala Val Arg Leu Phe Ile Glu Trp
        20                  25                  30

Leu Lys Asn Gly Gly Pro Ser Ser Gly Ala Pro Pro Ser
        35                  40                  45
```

<210> SEQ ID NO 43
<211> LENGTH: 48
<212> TYPE: PRT
<213> ORGANISM: Artificial Sequence
<220> FEATURE:
<223> OTHER INFORMATION: chemically synthesized peptide

<400> SEQUENCE: 43

```
His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Arg Lys Lys Arg Arg Gln Arg Arg
        35                  40                  45
```

<210> SEQ ID NO 44
<211> LENGTH: 40
<212> TYPE: PRT
<213> ORGANISM: Artificial Sequence
<220> FEATURE:
<223> OTHER INFORMATION: chemically synthesized peptide

<400> SEQUENCE: 44

```
Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln Arg
            20                  25                  30

Lys Lys Arg Arg Gln Arg Arg Arg
        35                  40
```

<210> SEQ ID NO 45
<211> LENGTH: 39
<212> TYPE: PRT
<213> ORGANISM: Artificial Sequence
<220> FEATURE:
<223> OTHER INFORMATION: chemically synthesized peptide

<400> SEQUENCE: 45

```
Val Thr His Arg Leu Ala Gly Leu Leu Ser Arg Ser Gly Gly Val Val
1               5                   10                  15

Lys Asn Asn Phe Val Pro Ile Asn Val Gly Ser Lys Ala Phe Arg Lys
            20                  25                  30

Lys Arg Arg Gln Arg Arg Arg
        35
```

<210> SEQ ID NO 46
<211> LENGTH: 61
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (16)..(21)

<400> SEQUENCE: 46

```
Tyr Arg Gln Ser Met Asn Asn Phe Gln Gly Leu Arg Ser Phe Gly Cys
1               5                   10                  15
```

```
Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
            35                  40                  45

Pro Gln Gly Tyr Arg Lys Arg Arg Gln Arg Arg
            50                  55                  60

<210> SEQ ID NO 47
<211> LENGTH: 29
<212> TYPE: PRT
<213> ORGANISM: Artificial Sequence
<220> FEATURE:
<223> OTHER INFORMATION: chemically synthesized peptide

<400> SEQUENCE: 47

Ala Arg Leu Asp Val Ala Ser Glu Phe Arg Lys Lys Trp Asn Lys Trp
1               5                   10                  15

Ala Leu Ser Arg Arg Lys Lys Arg Arg Gln Arg Arg Arg
            20                  25

<210> SEQ ID NO 48
<211> LENGTH: 47
<212> TYPE: PRT
<213> ORGANISM: Artificial Sequence
<220> FEATURE:
<223> OTHER INFORMATION: chemically synthesized peptide

<400> SEQUENCE: 48

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Arg Lys Arg Arg Gln Arg Arg Arg
            35                  40                  45

<210> SEQ ID NO 49
<211> LENGTH: 36
<212> TYPE: PRT
<213> ORGANISM: Artificial Sequence
<220> FEATURE:
<223> OTHER INFORMATION: chemically synthesized peptide

<400> SEQUENCE: 49

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Arg Lys Lys Arg Arg
            20                  25                  30

Gln Arg Arg Arg
        35

<210> SEQ ID NO 50
<211> LENGTH: 41
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (1)..(7)

<400> SEQUENCE: 50

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
```

```
                    20                  25                  30

Arg Lys Lys Arg Arg Gln Arg Arg
        35                  40

<210> SEQ ID NO 51
<211> LENGTH: 34
<212> TYPE: PRT
<213> ORGANISM: Artificial Sequence
<220> FEATURE:
<223> OTHER INFORMATION: chemically synthesized peptide

<400> SEQUENCE: 51

Val Leu Gly Lys Leu Ser Gln Glu Leu His Lys Leu Gln Thr Tyr Pro
1               5                   10                  15

Arg Thr Asn Thr Gly Ser Gly Thr Pro Arg Lys Lys Arg Arg Gln Arg
                20                  25                  30

Arg Arg

<210> SEQ ID NO 52
<211> LENGTH: 34
<212> TYPE: PRT
<213> ORGANISM: Artificial Sequence
<220> FEATURE:
<223> OTHER INFORMATION: chemically synthesized peptide

<400> SEQUENCE: 52

Phe Arg Val Asp Glu Glu Phe Gln Ser Pro Phe Ala Ser Gln Ser Arg
1               5                   10                  15

Gly Tyr Phe Leu Phe Arg Pro Arg Asn Arg Lys Lys Arg Arg Gln Arg
                20                  25                  30

Arg Arg

<210> SEQ ID NO 53
<211> LENGTH: 17
<212> TYPE: PRT
<213> ORGANISM: Artificial Sequence
<220> FEATURE:
<223> OTHER INFORMATION: chemically synthesized peptide

<400> SEQUENCE: 53

Tyr Phe Leu Phe Arg Pro Arg Asn Arg Lys Lys Arg Arg Gln Arg Arg
1               5                   10                  15

Arg

<210> SEQ ID NO 54
<211> LENGTH: 32
<212> TYPE: PRT
<213> ORGANISM: Artificial Sequence
<220> FEATURE:
<223> OTHER INFORMATION: chemically synthesized peptide

<400> SEQUENCE: 54

Tyr Lys Val Asn Glu Tyr Gln Arg Pro Val Ala Pro Ser Gly Gly Phe
1               5                   10                  15

Phe Leu Phe Arg Pro Arg Asn Arg Lys Lys Arg Arg Gln Arg Arg Arg
                20                  25                  30

<210> SEQ ID NO 55
<211> LENGTH: 17
<212> TYPE: PRT
<213> ORGANISM: Artificial Sequence
<220> FEATURE:
<223> OTHER INFORMATION: chemically synthesized peptide
<220> FEATURE:
```

```
<221> NAME/KEY: D-PHE
<222> LOCATION: (10)..(10)
<223> OTHER INFORMATION: d-phenylalanine
<220> FEATURE:
<221> NAME/KEY: D-TRP
<222> LOCATION: (13)..(13)
<223> OTHER INFORMATION: d-tryptophan
<220> FEATURE:
<221> NAME/KEY: THR-OL
<222> LOCATION: (17)..(17)
<223> OTHER INFORMATION: threonine-amino alchohol

<400> SEQUENCE: 55

Arg Lys Lys Arg Arg Gln Arg Arg Phe Cys Phe Trp Lys Thr Cys
1               5                   10                  15

Thr

<210> SEQ ID NO 56
<211> LENGTH: 17
<212> TYPE: PRT
<213> ORGANISM: Artificial Sequence
<220> FEATURE:
<223> OTHER INFORMATION: chemically synthesized peptide
<220> FEATURE:
<221> NAME/KEY: D-PHE
<222> LOCATION: (10)..(10)
<223> OTHER INFORMATION: d-phenylalanine
<220> FEATURE:
<221> NAME/KEY: D-TRP
<222> LOCATION: (13)..(13)
<223> OTHER INFORMATION: d-tryptophan
<220> FEATURE:
<221> NAME/KEY: THR-OL
<222> LOCATION: (17)..(17)
<223> OTHER INFORMATION: threonine-amino alchohol

<400> SEQUENCE: 56

Arg Lys Lys Arg Arg Gln Arg Arg Phe Cys Tyr Trp Lys Thr Cys
1               5                   10                  15

Thr

<210> SEQ ID NO 57
<211> LENGTH: 63
<212> TYPE: PRT
<213> ORGANISM: Artificial Sequence
<220> FEATURE:
<223> OTHER INFORMATION: chemically synthesized peptide
<220> FEATURE:
<221> NAME/KEY: P-GLU
<222> LOCATION: (1)..(1)
<223> OTHER INFORMATION: para-glutamic acid

<400> SEQUENCE: 57

Glu Thr Ser Gly Gly Pro Val Asp Ala Ser Ser Glu Tyr Gln Gln Glu
1               5                   10                  15

Leu Glu Arg Glu Leu Phe Lys Leu Lys Gln Met Phe Gly Asn Ala Asp
            20                  25                  30

Met Asn Thr Phe Pro Thr Phe Lys Phe Glu Asp Pro Lys Phe Glu Val
        35                  40                  45

Ile Glu Lys Pro Gln Ala Arg Lys Lys Arg Gln Arg Arg Arg
    50                  55                  60

<210> SEQ ID NO 58
<211> LENGTH: 86
<212> TYPE: PRT
<213> ORGANISM: Artificial Sequence
<220> FEATURE:
<223> OTHER INFORMATION: chemically synthesized peptide
```

```
<400> SEQUENCE: 58

Asn Lys Glu Leu Asp Pro Ile Gln Lys Leu Phe Val Asp Lys Ile Arg
1               5                   10                  15

Glu Tyr Lys Ser Lys Arg Gln Thr Ser Gly Gly Pro Val Asp Ala Ser
            20                  25                  30

Ser Glu Tyr Gln Gln Glu Leu Glu Arg Glu Leu Phe Lys Leu Lys Gln
        35                  40                  45

Met Phe Gly Asn Ala Asp Met Asn Thr Phe Pro Thr Phe Lys Phe Glu
    50                  55                  60

Asp Pro Lys Phe Glu Val Ile Glu Lys Pro Gln Ala Asn Arg Lys Lys
65                  70                  75                  80

Arg Arg Gln Arg Arg
                85

<210> SEQ ID NO 59
<211> LENGTH: 24
<212> TYPE: PRT
<213> ORGANISM: Artificial Sequence
<220> FEATURE:
<223> OTHER INFORMATION: chemically synthesized peptide
<220> FEATURE:
<221> NAME/KEY: ACETYL
<222> LOCATION: (1)..(1)
<223> OTHER INFORMATION: n-terminus acetyl

<400> SEQUENCE: 59

Lys Pro Ser Ser Pro Pro Glu Glu Arg Gln Ile Lys Ile Trp Phe Gln
1               5                   10                  15

Asn Arg Arg Met Lys Trp Lys Lys
            20

<210> SEQ ID NO 60
<211> LENGTH: 40
<212> TYPE: PRT
<213> ORGANISM: Artificial Sequence
<220> FEATURE:
<223> OTHER INFORMATION: chemically synthesized peptide

<400> SEQUENCE: 60

Met Ala Pro Arg Gly Phe Ser Cys Leu Leu Leu Leu Thr Ser Glu Ile
1               5                   10                  15

Asp Leu Pro Val Lys Arg Arg Ala Arg Gln Ile Lys Ile Trp Phe Gln
            20                  25                  30

Asn Arg Arg Met Lys Trp Lys Lys
            35                  40

<210> SEQ ID NO 61
<211> LENGTH: 40
<212> TYPE: PRT
<213> ORGANISM: Artificial Sequence
<220> FEATURE:
<223> OTHER INFORMATION: chemically synthesized peptide

<400> SEQUENCE: 61

Arg Gln Ile Lys Ile Trp Phe Gln Asn Arg Arg Met Lys Trp Lys Lys
1               5                   10                  15

Met Ala Pro Arg Gly Phe Ser Cys Leu Leu Leu Leu Thr Ser Glu Ile
            20                  25                  30

Asp Leu Pro Val Lys Arg Arg Ala
            35                  40

<210> SEQ ID NO 62
```

```
<211> LENGTH: 29
<212> TYPE: PRT
<213> ORGANISM: Artificial Sequence
<220> FEATURE:
<223> OTHER INFORMATION: chemically synthesized peptide
<220> FEATURE:
<221> NAME/KEY: P-GLU
<222> LOCATION: (1)..(1)
<223> OTHER INFORMATION: n-terminal para-glutamic acid

<400> SEQUENCE: 62

Glu Arg Pro Arg Leu Ser His Lys Gly Pro Met Pro Phe Arg Gln Ile
1               5                   10                  15

Lys Ile Trp Phe Gln Asn Arg Arg Met Lys Trp Lys Lys
            20                  25

<210> SEQ ID NO 63
<211> LENGTH: 52
<212> TYPE: PRT
<213> ORGANISM: Artificial Sequence
<220> FEATURE:
<223> OTHER INFORMATION: chemically synthesized peptide

<400> SEQUENCE: 63

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe Arg Gln Ile Lys Ile Trp Phe Gln Asn Arg Arg Met
        35                  40                  45

Lys Trp Lys Lys
    50

<210> SEQ ID NO 64
<211> LENGTH: 44
<212> TYPE: PRT
<213> ORGANISM: Artificial Sequence
<220> FEATURE:
<223> OTHER INFORMATION: chemically synthesized peptide
<220> FEATURE:
<221> NAME/KEY: SER-DES-OCTANOYL
<222> LOCATION: (3)..(3)
<223> OTHER INFORMATION: serine-des-octanoyl

<400> SEQUENCE: 64

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg Arg Gln Ile Lys
            20                  25                  30

Ile Trp Phe Gln Asn Arg Arg Met Lys Trp Lys Lys
        35                  40

<210> SEQ ID NO 65
<211> LENGTH: 44
<212> TYPE: PRT
<213> ORGANISM: Artificial Sequence
<220> FEATURE:
<223> OTHER INFORMATION: chemically synthesized peptide
<220> FEATURE:
<221> NAME/KEY: SER-OCTANOYL
<222> LOCATION: (3)..(3)
<223> OTHER INFORMATION: serine-octanoyl

<400> SEQUENCE: 65

Gly Ser Ser Phe Leu Ser Pro Glu His Gln Lys Ala Gln Gln Arg Lys
1               5                   10                  15
```

Glu Ser Lys Lys Pro Pro Ala Lys Leu Gln Pro Arg Gln Ile Lys
            20                  25                  30

Ile Trp Phe Gln Asn Arg Arg Met Lys Trp Lys Lys
            35                  40

<210> SEQ ID NO 66
<211> LENGTH: 44
<212> TYPE: PRT
<213> ORGANISM: Artificial Sequence
<220> FEATURE:
<223> OTHER INFORMATION: chemically synthesized peptide
<220> FEATURE:
<221> NAME/KEY: SER-OCTANYL
<222> LOCATION: (3)..(3)
<223> OTHER INFORMATION: serine-octanyl

<400> SEQUENCE: 66

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg Gln Ile Lys
            20                  25                  30

Ile Trp Phe Gln Asn Arg Arg Met Lys Trp Lys Lys
            35                  40

<210> SEQ ID NO 67
<211> LENGTH: 24
<212> TYPE: PRT
<213> ORGANISM: Artificial Sequence
<220> FEATURE:
<223> OTHER INFORMATION: chemically synthesized peptide

<400> SEQUENCE: 67

Asp Arg Val Tyr Ile His Pro Phe Arg Gln Ile Lys Ile Trp Phe Gln
1               5                   10                  15

Asn Arg Arg Met Lys Trp Lys Lys
            20

<210> SEQ ID NO 68
<211> LENGTH: 23
<212> TYPE: PRT
<213> ORGANISM: Artificial Sequence
<220> FEATURE:
<223> OTHER INFORMATION: chemically synthesized peptide

<400> SEQUENCE: 68

Asp Arg Val Tyr Ile His Pro Arg Gln Ile Lys Ile Trp Phe Gln Asn
1               5                   10                  15

Arg Arg Met Lys Trp Lys Lys
            20

<210> SEQ ID NO 69
<211> LENGTH: 22
<212> TYPE: PRT
<213> ORGANISM: Artificial Sequence
<220> FEATURE:
<223> OTHER INFORMATION: chemically synthesized peptide

<400> SEQUENCE: 69

Val Tyr Ile His Pro Phe Arg Gln Ile Lys Ile Trp Phe Gln Asn Arg
1               5                   10                  15

Arg Met Lys Trp Lys Lys
            20

<210> SEQ ID NO 70
<211> LENGTH: 21

```
<212> TYPE: PRT
<213> ORGANISM: Artificial Sequence
<220> FEATURE:
<223> OTHER INFORMATION: chemically synthesized peptide

<400> SEQUENCE: 70

His Trp Lys Trp Phe Arg Gln Ile Lys Ile Trp Phe Gln Asn Arg Arg
1               5                   10                  15

Met Lys Trp Lys Lys
            20

<210> SEQ ID NO 71
<211> LENGTH: 46
<212> TYPE: PRT
<213> ORGANISM: Artificial Sequence
<220> FEATURE:
<223> OTHER INFORMATION: chemically synthesized peptide

<400> SEQUENCE: 71

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Ile Lys Ile Trp Phe Gln Asn Arg Arg Met Lys Trp Lys Lys
        35                  40                  45

<210> SEQ ID NO 72
<211> LENGTH: 50
<212> TYPE: PRT
<213> ORGANISM: Artificial Sequence
<220> FEATURE:
<223> OTHER INFORMATION: chemically synthesized peptide

<400> SEQUENCE: 72

Arg Gln Ile Lys Ile Trp Phe Gln Asn Arg Arg Met Lys Trp Lys Lys
1               5                   10                  15

Ile Lys Pro Glu Ala Pro Gly Glu Asp Ala Ser Pro Glu Glu Leu Asn
            20                  25                  30

Arg Tyr Tyr Ala Ser Leu Arg His Tyr Leu Asn Leu Val Thr Arg Gln
        35                  40                  45

Arg Tyr
    50

<210> SEQ ID NO 73
<211> LENGTH: 29
<212> TYPE: PRT
<213> ORGANISM: Artificial Sequence
<220> FEATURE:
<223> OTHER INFORMATION: chemically synthesized peptide
<220> FEATURE:
<221> NAME/KEY: ACETYL
<222> LOCATION: (1)..(1)
<223> OTHER INFORMATION: n-terminus acetyl

<400> SEQUENCE: 73

Ser Tyr Ser Met Glu His Phe Arg Trp Gly Lys Pro Val Arg Gln Ile
1               5                   10                  15

Lys Ile Trp Phe Gln Asn Arg Arg Met Lys Trp Lys Lys
            20                  25

<210> SEQ ID NO 74
<211> LENGTH: 19
<212> TYPE: PRT
<213> ORGANISM: Artificial Sequence
<220> FEATURE:
```

```
<223> OTHER INFORMATION: chemically synthesized peptide
<220> FEATURE:
<221> NAME/KEY: DISULFID
<222> LOCATION: (7)..(16)

<400> SEQUENCE: 74

Trp Gln Val Arg Gln Ile Lys Ile Trp Phe Gln Asn Arg Arg Met Lys
1               5                   10                  15

Trp Lys Lys

<210> SEQ ID NO 75
<211> LENGTH: 30
<212> TYPE: PRT
<213> ORGANISM: Artificial Sequence
<220> FEATURE:
<223> OTHER INFORMATION: chemically synthesized peptide

<400> SEQUENCE: 75

Glu Gln Arg Leu Gly Asn Gln Trp Ala Val Gly His Leu Met Arg Gln
1               5                   10                  15

Ile Lys Ile Trp Phe Gln Asn Arg Arg Met Lys Trp Lys Lys
            20                  25                  30

<210> SEQ ID NO 76
<211> LENGTH: 67
<212> TYPE: PRT
<213> ORGANISM: Artificial Sequence
<220> FEATURE:
<223> OTHER INFORMATION: chemically synthesized peptide

<400> SEQUENCE: 76

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Pro Lys Thr Arg Gln Ile Lys Ile Trp Phe Gln Asn Arg Arg Met Lys
    50                  55                  60

Trp Lys Lys
65

<210> SEQ ID NO 77
<211> LENGTH: 44
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (7)..(23)

<400> SEQUENCE: 77

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Gln Ile Lys
            20                  25                  30

Ile Trp Phe Gln Asn Arg Arg Met Lys Trp Lys Lys
        35                  40

<210> SEQ ID NO 78
<211> LENGTH: 48
<212> TYPE: PRT
<213> ORGANISM: Artificial Sequence
```

```
<220> FEATURE:
<223> OTHER INFORMATION: chemically synthesized peptide
<220> FEATURE:
<221> NAME/KEY: DISULFID
<222> LOCATION: (10)..(26)

<400> SEQUENCE: 78

Ser Pro Lys Met Val Gln Gly Ser Gly Cys Phe Gly Arg Lys Met Asp
1               5                   10                  15

Arg Ile Ser Ser Ser Gly Leu Gly Cys Lys Val Leu Arg Arg His
            20                  25                  30

Arg Gln Ile Lys Ile Trp Phe Gln Asn Arg Arg Met Lys Trp Lys Lys
        35                  40                  45

<210> SEQ ID NO 79
<211> LENGTH: 48
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (10)..(26)

<400> SEQUENCE: 79

Asn Ser Lys Met Ala His Ser Ser Cys Phe Gly Gln Lys Ile Asp
1               5                   10                  15

Arg Ile Gly Ala Val Ser Arg Leu Gly Cys Asp Gly Leu Arg Leu Phe
            20                  25                  30

Arg Gln Ile Lys Ile Trp Phe Gln Asn Arg Arg Met Lys Trp Lys Lys
        35                  40                  45

<210> SEQ ID NO 80
<211> LENGTH: 64
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (14)..(32)
<220> FEATURE:
<221> NAME/KEY: DISULFID
<222> LOCATION: (20)..(40)
<220> FEATURE:
<221> NAME/KEY: DISULFID
<222> LOCATION: (34)..(47)

<400> SEQUENCE: 80

Val Pro Ile Tyr Glu Lys Lys Tyr Gly Gln Val Pro Met Cys Asp Ala
1               5                   10                  15

Gly Glu Gln Cys Ala Val Arg Lys Gly Ala Arg Ile Gly Lys Leu Cys
            20                  25                  30

Asp Cys Pro Arg Gly Thr Ser Cys Asn Ser Phe Leu Leu Lys Cys Leu
        35                  40                  45

Arg Gln Ile Lys Ile Trp Phe Gln Asn Arg Arg Met Lys Trp Lys Lys
    50                  55                  60

<210> SEQ ID NO 81
<211> LENGTH: 66
<212> TYPE: PRT
<213> ORGANISM: Artificial Sequence
<220> FEATURE:
<223> OTHER INFORMATION: chemically synthesized peptide

<400> SEQUENCE: 81
```

```
Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
            20                  25                  30

Ala Phe Cys Tyr Cys Arg Lys Leu Gly Thr Ala Met Asn Pro Cys Ser
        35                  40                  45

Arg Thr Arg Gln Ile Lys Ile Trp Phe Gln Asn Arg Arg Met Lys Trp
    50                  55                  60

Lys Lys
65
```

<210> SEQ ID NO 82
<211> LENGTH: 47
<212> TYPE: PRT
<213> ORGANISM: Artificial Sequence
<220> FEATURE:
<223> OTHER INFORMATION: chemically synthesized peptide

<400> SEQUENCE: 82

```
Arg Gln Ile Lys Ile Trp Phe Gln Asn Arg Arg Met Lys Trp Lys Lys
1               5                   10                  15

His Ala Glu Gly Thr Phe Thr Ser Asp Val Ser Ser Tyr Leu Glu Gly
            20                  25                  30

Gln Ala Ala Lys Glu Phe Ile Ala Trp Leu Val Lys Gly Arg Gly
        35                  40                  45
```

<210> SEQ ID NO 83
<211> LENGTH: 47
<212> TYPE: PRT
<213> ORGANISM: Artificial Sequence
<220> FEATURE:
<223> OTHER INFORMATION: chemically synthesized peptide

<400> SEQUENCE: 83

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Gln Ile Lys Ile Trp Phe Gln Asn Arg Arg Met Lys Trp Lys Lys
        35                  40                  45
```

<210> SEQ ID NO 84
<211> LENGTH: 53
<212> TYPE: PRT
<213> ORGANISM: Artificial Sequence
<220> FEATURE:
<223> OTHER INFORMATION: chemically synthesized peptide

<400> SEQUENCE: 84

```
Glu Gly Thr Phe Thr Ser Asp Leu Ser Lys Gln Met Glu Glu Glu Ala
1               5                   10                  15

Val Arg Leu Phe Ile Glu Thr Leu Lys Asn Gly Gly Pro Ser Ser Gly
            20                  25                  30

Ala Pro Pro Pro Ser Arg Gln Ile Lys Ile Trp Phe Gln Asn Arg Arg
        35                  40                  45

Met Lys Trp Lys Lys
    50
```

<210> SEQ ID NO 85
<211> LENGTH: 53
<212> TYPE: PRT
<213> ORGANISM: Artificial Sequence

```
<220> FEATURE:
<223> OTHER INFORMATION: chemically synthesized peptide

<400> SEQUENCE: 85

Arg Gln Ile Lys Ile Trp Phe Gln Asn Arg Arg Met Lys Trp Lys Lys
1               5                   10                  15

Glu Gly Thr Phe Thr Ser Asp Leu Ser Lys Gln Met Glu Glu Glu Ala
                20                  25                  30

Val Arg Leu Phe Ile Glu Trp Leu Lys Asn Gly Gly Pro Ser Ser Gly
            35                  40                  45

Ala Pro Pro Ser
    50

<210> SEQ ID NO 86
<211> LENGTH: 55
<212> TYPE: PRT
<213> ORGANISM: Artificial Sequence
<220> FEATURE:
<223> OTHER INFORMATION: chemically synthesized peptide

<400> SEQUENCE: 86

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Arg Gln Ile Lys Ile Trp Phe Gln Asn
            35                  40                  45

Arg Arg Met Lys Trp Lys Lys
    50                  55

<210> SEQ ID NO 87
<211> LENGTH: 47
<212> TYPE: PRT
<213> ORGANISM: Artificial Sequence
<220> FEATURE:
<223> OTHER INFORMATION: chemically synthesized peptide

<400> SEQUENCE: 87

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln Arg
                20                  25                  30

Gln Ile Lys Ile Trp Phe Gln Asn Arg Met Lys Trp Lys Lys
            35                  40                  45

<210> SEQ ID NO 88
<211> LENGTH: 46
<212> TYPE: PRT
<213> ORGANISM: Artificial Sequence
<220> FEATURE:
<223> OTHER INFORMATION: chemically synthesized peptide

<400> SEQUENCE: 88

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe Arg Gln
                20                  25                  30

Ile Lys Ile Trp Phe Gln Asn Arg Arg Met Lys Trp Lys Lys
            35                  40                  45

<210> SEQ ID NO 89
<211> LENGTH: 68
```

```
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (16)..(21)

<400> SEQUENCE: 89

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr Arg Gln Ile Lys Ile Trp Phe Gln Asn Arg Arg Met
    50                  55                  60

Lys Trp Lys Lys
65

<210> SEQ ID NO 90
<211> LENGTH: 36
<212> TYPE: PRT
<213> ORGANISM: Artificial Sequence
<220> FEATURE:
<223> OTHER INFORMATION: chemically synthesized peptide

<400> SEQUENCE: 90

Ala Arg Leu Asp Val Ala Ser Glu Phe Arg Lys Lys Trp Asn Lys Trp
1               5                   10                  15

Ala Leu Ser Arg Arg Gln Ile Lys Ile Trp Phe Gln Asn Arg Arg Met
            20                  25                  30

Lys Trp Lys Lys
        35

<210> SEQ ID NO 91
<211> LENGTH: 54
<212> TYPE: PRT
<213> ORGANISM: Artificial Sequence
<220> FEATURE:
<223> OTHER INFORMATION: chemically synthesized peptide

<400> SEQUENCE: 91

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Arg Gln Ile Lys Ile Trp Phe Gln Asn Arg
        35                  40                  45

Arg Met Lys Trp Lys Lys
    50

<210> SEQ ID NO 92
<211> LENGTH: 43
<212> TYPE: PRT
<213> ORGANISM: Artificial Sequence
<220> FEATURE:
<223> OTHER INFORMATION: chemically synthesized peptide

<400> SEQUENCE: 92

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Arg Gln Ile Tyr Ile
```

```
                    20                  25                  30

Trp Phe Gln Asn Arg Arg Met Lys Trp Lys Lys
        35                  40

<210> SEQ ID NO 93
<211> LENGTH: 56
<212> TYPE: PRT
<213> ORGANISM: Artificial Sequence
<220> FEATURE:
<223> OTHER INFORMATION: chemically synthesized peptide
<220> FEATURE:
<221> NAME/KEY: DISULFID
<222> LOCATION: (1)..(7)

<400> SEQUENCE: 93

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

Arg Gln Ile Lys Ile Trp Phe Gln Asn Arg Arg Met Lys Trp Lys Lys
        35                  40                  45

Lys Lys Arg Arg Gln Arg Arg
    50                  55

<210> SEQ ID NO 94
<211> LENGTH: 41
<212> TYPE: PRT
<213> ORGANISM: Artificial Sequence
<220> FEATURE:
<223> OTHER INFORMATION: chemically synthesized peptide

<400> SEQUENCE: 94

Val Leu Gly Lys Leu Ser Gln Glu Leu His Lys Leu Gln Thr Tyr Pro
1               5                   10                  15

Arg Thr Asn Thr Gly Ser Gly Thr Pro Arg Gln Ile Lys Ile Trp Phe
            20                  25                  30

Gln Asn Arg Arg Met Lys Trp Lys Lys
        35                  40

<210> SEQ ID NO 95
<211> LENGTH: 41
<212> TYPE: PRT
<213> ORGANISM: Artificial Sequence
<220> FEATURE:
<223> OTHER INFORMATION: chemically synthesized peptide

<400> SEQUENCE: 95

Phe Arg Val Asp Glu Glu Phe Gln Ser Pro Phe Ala Ser Gln Ser Arg
1               5                   10                  15

Gly Tyr Phe Leu Phe Arg Pro Arg Asn Arg Gln Ile Lys Ile Trp Phe
            20                  25                  30

Gln Asn Arg Arg Met Lys Trp Lys Lys
        35                  40

<210> SEQ ID NO 96
<211> LENGTH: 24
<212> TYPE: PRT
<213> ORGANISM: Artificial Sequence
<220> FEATURE:
<223> OTHER INFORMATION: chemically synthesized peptide

<400> SEQUENCE: 96

Tyr Phe Leu Phe Arg Pro Arg Asn Arg Gln Ile Lys Ile Trp Phe Gln
1               5                   10                  15
```

```
Asn Arg Arg Met Lys Trp Lys Lys
            20

<210> SEQ ID NO 97
<211> LENGTH: 39
<212> TYPE: PRT
<213> ORGANISM: Artificial Sequence
<220> FEATURE:
<223> OTHER INFORMATION: chemically synthesized peptide

<400> SEQUENCE: 97

Tyr Lys Val Asn Glu Tyr Gln Gly Pro Val Ala Pro Ser Gly Gly Phe
 1               5                  10                  15

Phe Leu Phe Arg Pro Arg Asn Arg Gln Ile Lys Ile Trp Phe Gln Asn
            20                  25                  30

Arg Arg Met Lys Trp Lys Lys
            35

<210> SEQ ID NO 98
<211> LENGTH: 23
<212> TYPE: PRT
<213> ORGANISM: Artificial Sequence
<220> FEATURE:
<223> OTHER INFORMATION: chemically synthesized peptide
<220> FEATURE:
<221> NAME/KEY: D-PHE
<222> LOCATION: (16)..(16)
<223> OTHER INFORMATION: d-phenylalanine
<220> FEATURE:
<221> NAME/KEY: D-TRP
<222> LOCATION: (19)..(19)
<223> OTHER INFORMATION: d-tryptophan
<220> FEATURE:
<221> NAME/KEY: THR-OL
<222> LOCATION: (21)..(21)
<223> OTHER INFORMATION: threonine-amino alchohol

<400> SEQUENCE: 98

Arg Gln Ile Lys Ile Trp Phe Gln Asn Arg Met Lys Trp Lys Lys Phe
 1               5                  10                  15

Cys Phe Trp Lys Thr Cys Thr
            20

<210> SEQ ID NO 99
<211> LENGTH: 24
<212> TYPE: PRT
<213> ORGANISM: Artificial Sequence
<220> FEATURE:
<223> OTHER INFORMATION: chemically synthesized peptide
<220> FEATURE:
<221> NAME/KEY: D-PHE
<222> LOCATION: (17)..(17)
<223> OTHER INFORMATION: d-phenylalanine
<220> FEATURE:
<221> NAME/KEY: D-TRP
<222> LOCATION: (20)..(20)
<223> OTHER INFORMATION: d-tryptophan
<220> FEATURE:
<221> NAME/KEY: THR-OL
<222> LOCATION: (24)..(24)
<223> OTHER INFORMATION: threonine-amino alchohol

<400> SEQUENCE: 99

Arg Gln Ile Lys Ile Trp Phe Gln Asn Arg Arg Met Lys Trp Lys Lys
 1               5                  10                  15

Phe Cys Tyr Trp Lys Thr Cys Thr
            20
```

```
<210> SEQ ID NO 100
<211> LENGTH: 54
<212> TYPE: PRT
<213> ORGANISM: Artificial Sequence
<220> FEATURE:
<223> OTHER INFORMATION: chemically synthesized peptide
<220> FEATURE:
<221> NAME/KEY: P-GLU
<222> LOCATION: (1)..(1)
<223> OTHER INFORMATION: n-terminal-para-glutamic acid

<400> SEQUENCE: 100

Glu Thr Ser Gly Gly Pro Val Asp Ala Ser Ser Glu Tyr Gln Gln Glu
1               5                   10                  15

Leu Glu Arg Glu Leu Phe Lys Leu Lys Gln Met Phe Gly Asn Ala Asp
            20                  25                  30

Met Asn Thr Phe Pro Thr Phe Lys Phe Glu Asp Pro Lys Phe Glu Val
        35                  40                  45

Ile Glu Lys Pro Gln Ala
    50

<210> SEQ ID NO 101
<211> LENGTH: 77
<212> TYPE: PRT
<213> ORGANISM: Artificial Sequence
<220> FEATURE:
<223> OTHER INFORMATION: chemically synthesized peptide

<400> SEQUENCE: 101

Asn Lys Glu Leu Asp Pro Ile Gln Lys Leu Phe Val Asp Lys Ile Arg
1               5                   10                  15

Glu Tyr Lys Ser Lys Arg Gln Thr Ser Gly Gly Pro Val Asp Ala Ser
            20                  25                  30

Ser Glu Tyr Gln Gln Glu Leu Glu Arg Glu Leu Phe Lys Leu Lys Gln
        35                  40                  45

Met Phe Gly Asn Ala Asp Met Asn Thr Phe Pro Thr Phe Lys Phe Glu
    50                  55                  60

Asp Pro Lys Phe Glu Val Ile Glu Lys Pro Gln Ala Asn
65                  70                  75

<210> SEQ ID NO 102
<211> LENGTH: 9
<212> TYPE: PRT
<213> ORGANISM: Human immunodeficiency virus type 1

<400> SEQUENCE: 102

Arg Lys Lys Arg Arg Gln Arg Arg Arg
1               5

<210> SEQ ID NO 103
<211> LENGTH: 16
<212> TYPE: PRT
<213> ORGANISM: Drosophila antennapedia homeo

<400> SEQUENCE: 103

Arg Gln Ile Lys Ile Trp Phe Gln Asn Arg Arg Met Lys Trp Lys Lys
1               5                   10                  15

<210> SEQ ID NO 104
<211> LENGTH: 57
<212> TYPE: PRT
<213> ORGANISM: Human immunodeficiency virus type 1

<400> SEQUENCE: 104
```

-continued

```
Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg Ala His Gln Asn
            20                  25                  30

Ser Gln Thr His Gln Ala Ser Leu Ser Lys Gln Pro Thr Ser Gln Pro
        35                  40                  45

Arg Gly Asp Pro Thr Gly Pro Lys Glu
    50                  55

<210> SEQ ID NO 105
<211> LENGTH: 57
<212> TYPE: PRT
<213> ORGANISM: Human Immunodeficiency virus type 1
<220> FEATURE:
<221> NAME/KEY: ACETAMIDOMETHYL
<222> LOCATION: (1)..(57)
<223> OTHER INFORMATION: positions 1, 5,
<220> FEATURE:
<221> NAME/KEY: TRITYL
<222> LOCATION: (1)..(57)
<223> OTHER INFORMATION: side chain protecting group positions 2, 4, 6,
      25, 30, 31, 32, 36, 37, 43,
<220> FEATURE:
<221> NAME/KEY: T-BUTYL
<222> LOCATION: (1)..(57)
<223> OTHER INFORMATION: side chain protecting group positions 11, 17,
      18, 33, 35, 39, 41
<220> FEATURE:
<221> NAME/KEY: TERT-BUTYLOXYCARBONYL
<222> LOCATION: (1)..(57)
<223> OTHER INFORMATION: side chain protecting group positions 12, 21,
      22, 42
<220> FEATURE:
<221> NAME/KEY: 4-PYRROLEPHENYLACYL
<222> LOCATION: (1)..(57)
<223> OTHER INFORMATION: side chain protecting group positions 20, 22,
      23, 24, 26, 27, 28,
<220> FEATURE:
<221> NAME/KEY: CYCLOHEXYL-ESTER
<222> LOCATION: (1)..(57)
<223> OTHER INFORMATION: side chain protecting group positions 51, 57
<220> FEATURE:
<221> NAME/KEY: TOSYL
<222> LOCATION: (1)..(57)
<223> OTHER INFORMATION: side chain protecting group position 49
<220> FEATURE:
<221> NAME/KEY: BENZYL
<222> LOCATION: (1)..(57)
<223> OTHER INFORMATION: side chain protecting group positions 45, 46,
      53
<220> FEATURE:
<221> NAME/KEY: 2-CHLOROBENYZLOXYCARBONYL
<222> LOCATION: (1)..(57)
<223> OTHER INFORMATION: side chain protecting group position 56

<400> SEQUENCE: 105

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg Ala His Gln Asn
            20                  25                  30

Ser Gln Thr His Gln Ala Ser Leu Ser Lys Gln Pro Thr Ser Gln Pro
        35                  40                  45

Arg Gly Asp Pro Thr Gly Pro Lys Glu
    50                  55

<210> SEQ ID NO 106
<211> LENGTH: 57
<212> TYPE: PRT
<213> ORGANISM: Human immunodeficiency virus type 1
<220> FEATURE:
<221> NAME/KEY: ACETAMIDOMETHYL
```

```
<222> LOCATION: (1)..(1)
<220> FEATURE:
<221> NAME/KEY: ACETAMIDOMETHYL
<222> LOCATION: (5)..(5)

<400> SEQUENCE: 106

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg Ala His Gln Asn
            20                  25                  30

Ser Gln Thr His Gln Ala Ser Leu Ser Lys Gln Pro Thr Ser Gln Pro
        35                  40                  45

Arg Gly Asp Pro Thr Gly Pro Lys Glu
    50                  55

<210> SEQ ID NO 107
<211> LENGTH: 37
<212> TYPE: PRT
<213> ORGANISM: Human immunodeficiency virus type 1

<400> SEQUENCE: 107

Gly Arg Lys Lys Arg Arg Gln Arg Arg Arg Ala His Gln Asn Ser Gln
1               5                   10                  15

Thr His Gln Ala Ser Leu Ser Lys Gln Pro Thr Ser Gln Pro Arg Gly
            20                  25                  30

Asp Pro Thr Gly Pro
        35

<210> SEQ ID NO 108
<211> LENGTH: 29
<212> TYPE: PRT
<213> ORGANISM: Human immunodeficiency virus type 1

<400> SEQUENCE: 108

Ala His Gln Asn Ser Gln Thr His Gln Ala Ser Leu Ser Lys Gln Pro
1               5                   10                  15

Thr Ser Gln Pro Arg Gly Asp Pro Thr Gly Pro Lys Glu
            20                  25

<210> SEQ ID NO 109
<211> LENGTH: 25
<212> TYPE: PRT
<213> ORGANISM: Human immunodeficiency virus type 1

<400> SEQUENCE: 109

Ser Gln Thr His Gln Ala Ser Leu Ser Lys Gln Pro Thr Ser Gln Pro
1               5                   10                  15

Arg Gly Asp Pro Thr Gly Pro Lys Glu
            20                  25

<210> SEQ ID NO 110
<211> LENGTH: 20
<212> TYPE: PRT
<213> ORGANISM: Human immunodeficiency virus type 1

<400> SEQUENCE: 110

Asn Ser Gln Thr His Gln Ala Ser Leu Ser Lys Gln Pro Thr Ser Gln
1               5                   10                  15

Pro Arg Gly Asp
        20

<210> SEQ ID NO 111
```

```
<211> LENGTH: 20
<212> TYPE: PRT
<213> ORGANISM: Human immunodeficiency virus type 1

<400> SEQUENCE: 111

Lys Ala Leu Gly Ile Ser Tyr Gly Arg Lys Lys Arg Arg Gln Arg Arg
1               5                   10                  15

Arg Ala His Gln
        20

<210> SEQ ID NO 112
<211> LENGTH: 9
<212> TYPE: PRT
<213> ORGANISM: Artificial Sequence
<220> FEATURE:
<223> OTHER INFORMATION: chemically synthesized peptide

<400> SEQUENCE: 112

Arg Arg Arg Arg Arg Arg Arg Arg Arg
1               5

<210> SEQ ID NO 113
<211> LENGTH: 18
<212> TYPE: PRT
<213> ORGANISM: Human Immunodeficiency virus type 1
<220> FEATURE:
<221> NAME/KEY: DISULFID
<222> LOCATION: (1)..(5)
<220> FEATURE:
<221> NAME/KEY: DISULFID
<222> LOCATION: (2)..(8)

<400> SEQUENCE: 113

Cys Cys Phe His Cys Gln Val Cys Phe Ile Thr Lys Ala Leu Gly Ile
1               5                   10                  15

Ser Tyr

<210> SEQ ID NO 114
<211> LENGTH: 57
<212> TYPE: PRT
<213> ORGANISM: Human immunodeficiency virus type 1
<220> FEATURE:
<221> NAME/KEY: DISULFID
<222> LOCATION: (1)..(5)
<220> FEATURE:
<221> NAME/KEY: DISULFID
<222> LOCATION: (2)..(8)

<400> SEQUENCE: 114

Cys Cys Phe His Cys Gln Val Cys Phe Ile Thr Lys Ala Leu Gly Ile
1               5                   10                  15

Ser Tyr Gly Arg Lys Lys Arg Arg Gln Arg Arg Arg Ala His Gln Asn
            20                  25                  30

Ser Gln Thr His Gln Ala Ser Leu Ser Lys Gln Pro Thr Ser Gln Pro
        35                  40                  45

Arg Gly Asp Pro Thr Gly Pro Lys Glu
    50                  55

<210> SEQ ID NO 115
<211> LENGTH: 31
<212> TYPE: PRT
<213> ORGANISM: Human immunodeficiency virus type 1
<220> FEATURE:
<221> NAME/KEY: DISULFID
<222> LOCATION: (3)..(6)

<400> SEQUENCE: 115
```

-continued

```
Phe His Cys Gln Val Cys Phe Ile Thr Lys Ala Leu Gly Ile Ser Tyr
1               5                   10                  15

Gly Arg Lys Lys Arg Arg Gln Arg Arg Arg Ala His Gln Asn Ser
            20                  25                  30
```